(12) United States Patent
Parrott et al.

(10) Patent No.: US 11,910,838 B2
(45) Date of Patent: *Feb. 27, 2024

(54) HOT WIRE ANEMOMETER AIR FLOW MEASUREMENT, PUFF DETECTION AND AMBIENT TEMPERATURE TRACKING

(71) Applicant: Altria Client Services LLC, Richmond, VA (US)

(72) Inventors: Adam Parrott, Richmond, VA (US); Niall Gallagher, Richmond, VA (US); Raymond W. Lau, Richmond, VA (US); Eric Hawes, Glen Allen, VA (US); Ryan Newcomb, Richmond, VA (US); Terry Bache, Richmond, VA (US); Rangaraj S. Sundar, Richmond, VA (US); Jarrett Keen, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 387 days.

This patent is subject to a terminal disclaimer.

(21) Appl. No.: 16/749,640

(22) Filed: Jan. 22, 2020

(65) Prior Publication Data

US 2021/0219621 A1 Jul. 22, 2021

(51) Int. Cl.
*A24F 40/51* (2020.01)
*A24F 40/44* (2020.01)
(Continued)

(52) U.S. Cl.
CPC .............. *A24F 40/51* (2020.01); *A24F 40/44* (2020.01); *A24F 40/46* (2020.01); *A24F 40/57* (2020.01); *G01K 13/00* (2013.01); *G01P 5/02* (2013.01)

(58) Field of Classification Search
CPC .......... A24F 40/50; A24F 40/00; A24F 40/51; A24F 40/57; G01P 5/02; G01P 5/10; A61M 2016/0021; G01K 13/00
See application file for complete search history.

(56) References Cited

U.S. PATENT DOCUMENTS 4,487,063 A 12/1984 Hopper
5,392,768 A 2/1995 Johansson et al.
(Continued)

FOREIGN PATENT DOCUMENTS

DE 3706622 A1 9/1988
DE 102005056706 A1 5/2007
WO WO-2018/027189 A2 2/2018

OTHER PUBLICATIONS

K. Nouman, Z. Asim and K. Qasim, "Comprehensive Study on Performance of PID Controller and its Applications," 2018 2nd IEEE Advanced Information Management, Communicates, Electronic and Automation Control Conference (IMCEC), 2018, pp. 1574-1579, doi: 10.1109/IMCEC.2018.8469267. (Year: 2018).*

(Continued)

*Primary Examiner* — Kelly M Gambetta
*Assistant Examiner* — Stephanie Lynn Moore
(74) *Attorney, Agent, or Firm* — Harness, Dickey & Pierce, P.L.C.

(57) ABSTRACT

A method of controlling a hot wire anemometer (HWA) of a nicotine e-vaping device includes controlling, by a first PID controller, a level of power applied by the nicotine e-vaping device to the HWA based on a temperature of a heated element of the HWA and a temperature setpoint; generating a puff detection signal indicating whether or not a puff is currently occurring with respect to the nicotine e-vaping device; and while the puff detection signal indicates that a puff is not currently occurring with respect to the nicotine e-vaping device, detecting, by a second PID con- (Continued)

troller, a change in an ambient temperature of the HWA, and controlling, by the second PID controller, the temperature setpoint such that the temperature setpoint changes in response to the detected change in the ambient temperature of the HWA.

20 Claims, 33 Drawing Sheets

(51) Int. Cl.
*A24F 40/46* (2020.01)
*A24F 40/57* (2020.01)
*A61M 11/04* (2006.01)
*G01K 13/00* (2021.01)
*G01P 5/02* (2006.01)

(56) References Cited

U.S. PATENT DOCUMENTS

| | | |
|---|---|---|
| 5,595,706 A | 1/1997 | Sikka et al. |
| 6,338,271 B1 | 1/2002 | Stark |
| 6,474,155 B1 | 11/2002 | Berkcan et al. |
| 6,813,570 B2 | 11/2004 | Gee |
| 7,140,263 B2 | 11/2006 | Beversdorf |
| 7,320,459 B2 | 1/2008 | Johns |
| 7,653,503 B2 | 1/2010 | Mangalam et al. |
| 7,823,444 B2 | 11/2010 | Zschernack et al. |
| 8,413,503 B2 | 4/2013 | Graboi et al. |
| 8,650,947 B2 | 2/2014 | Lopez et al. |
| 8,733,349 B2 | 5/2014 | Bath et al. |
| 8,905,024 B2 | 12/2014 | Jafari et al. |
| 9,078,473 B2 | 7/2015 | Worm et al. |
| 9,176,163 B2 | 11/2015 | Heath et al. |
| 9,239,257 B2 | 1/2016 | Olin |
| 2005/0075804 A1 | 4/2005 | Gee |
| 2014/0270727 A1 | 9/2014 | Ampolini et al. |
| 2016/0021930 A1 | 1/2016 | Minskoff et al. |
| 2016/0033545 A1 | 2/2016 | Heath et al. |
| 2018/0000160 A1* | 1/2018 | Taschner ............. A24F 40/46 |
| 2018/0104214 A1 | 4/2018 | Raichman |
| 2018/0116292 A1 | 5/2018 | Atkins et al. |
| 2019/0104764 A1 | 4/2019 | Tucker et al. |
| 2020/0229509 A1 | 7/2020 | Griscik et al. |
| 2020/0405980 A1 | 12/2020 | Griscik et al. |

OTHER PUBLICATIONS

P.G.S.A Bandara "A Constant Current Hotwire Anemometer" University of Peradeniya Department of Physics, A project report Submitted in Partial Fulfillment of the Requirement of the Project for special degree of Bachelor of Science in physics, 2010/2011.

L.V. Araujo et al. "A controlled-temperature hot-wire anemometer with voltage feedback linearization" Department of Computer Engineering and Automation, Federal University of Rio Grande do Norte (UFRN) Natal, RN, Brazil.

International Search Report and Written Opinion for International Application No. PCT/EP2021/051521 dated Apr. 12, 2021.

Li et al: "The development of a pulsed multi-element hot-wire anemometer", Measurement Science and Technology, IOP, Bristol, GB, vol. 6, No. 8, Aug. 1, 1995 (Aug. 1, 1995), pp. 1175-1185, XP020066006.

International Search Report and Written Opinion for International Application No. PCT/US2021/013340 dated May 3, 2021.

International Preliminary Report on Patentability dated Dec. 16, 2021, issued in corresponding International Application No. PCT/EP2021/051521.

Office Action dated Jun. 14, 2022 issued in corresponding U.S. Appl. No. 16/749,692.

International Preliminary Report on Patentability and Written Opinion dated Aug. 4, 2022 issued in corresponding international patent application No. PCT/US2021/013340.

Final Office Action for U.S. Appl. No. 16/749,692, dated Nov. 1, 2022.

Non-Final Office Action Corresponding to related U.S. Appl. No. 16/749,692, dated May 16, 2023.

Final Office Action Corresponding to related U.S. Appl. No. 16/749,692, dated Aug. 10, 2023.

Notice of Allowance Corresponding to related U.S. Appl. No. 16/749,692, dated Oct. 27, 2023.

* cited by examiner

HOT WIRE ANEMOMETER AIR FLOW MEASUREMENT, PUFF DETECTION AND AMBIENT TEMPERATURE TRACKING

BACKGROUND

Field

The present disclosure relates to nicotine electronic vapor devices including self-contained articles including nicotine pre-vapor formulations.

Description of Related Art

Nicotine electronic vaping devices are used to vaporize a nicotine pre-vapor formulation material into a nicotine vapor. These nicotine electronic vaping devices may be referred to as nicotine e-vaping devices. Nicotine e-vaping devices include a heater which vaporizes the nicotine pre-vapor formulation material to produce nicotine vapor. A nicotine e-vaping device may include several e-vaping elements including a power source, a cartridge or e-vaping tank including the heater and along with a reservoir capable of holding the nicotine pre-vapor formulation material.

SUMMARY

According to at least some example embodiments, a method of controlling a hot wire anemometer (HWA) of a nicotine e-vaping device includes controlling, by a first PID controller, a level of power applied by the nicotine e-vaping device to the HWA based on a temperature of a heated element of the HWA and a temperature setpoint; generating a puff detection signal indicating whether or not a puff is currently occurring with respect to the nicotine e-vaping device; and while the puff detection signal indicates that a puff is not currently occurring with respect to the nicotine e-vaping device, detecting, by a second PID controller, a change in an ambient temperature of the HWA; and controlling, by the second PID controller, the temperature setpoint such that the temperature setpoint changes in response to the detected change in the ambient temperature of the HWA.

The controlling of the level of power applied by the nicotine e-vaping device to the HWA may include generating, by the first PID controller, a drive signal setting value, the level of power applied by the nicotine e-vaping device to the HWA being based on the drive signal setting value.

The method may further include, while the puff detection signal indicates that a puff is currently occurring with respect to the nicotine e-vaping device, determining a flow rate of air flowing around the HWA based on the drive signal setting value.

The generating of the puff detection signal may include determining a gradient of the drive signal setting value; and generating the puff detection signal based on the determined gradient of the drive signal setting value.

The method may further include generating a pulse width modulated (PWM) drive signal based on the drive signal setting value; and applying the power to the HWA by applying the PWM drive signal to the HWA.

The generating of the PWM drive signal may include generating the PWM drive signal such that a duty cycle of the PWM is controlled based on the drive signal setting value.

The generating of the drive signal setting value may include generating, by the first PID controller, the drive signal setting value based on a difference between the temperature of a heated element of the HWA and the temperature setpoint.

The detecting of the change in the ambient temperature of the HWA may include detecting, by the second PID controller, the change in the ambient temperature of the HWA based on a difference between the drive signal setting value and a drive signal setting value setpoint.

The detecting of the change in the ambient temperature of the HWA may include detecting, by the second PID controller, the change in the ambient temperature of the HWA based on a difference between the drive signal setting value and a drive signal setting value setpoint.

The controlling of the temperature setpoint may include increasing, by the second PID controller, the temperature setpoint in response to detecting an increase in the ambient temperature of the HWA; and decreasing, by the second PID controller, the temperature setpoint in response to detecting a decrease in the ambient temperature of the HWA.

According to at least some example embodiments, a nicotine e-vaping device includes a nicotine pre-vapor formulation storage portion for storing a nicotine pre-vapor formulation; a heater configured to generate a nicotine vapor by heating the nicotine pre-vapor formulation; a hot wire anemometer (HWA); a first PID controller configured to control a level of power applied by the nicotine e-vaping device to the HWA based on a temperature of a heated element of the HWA and a temperature setpoint; a puff detection signal generator configured to generate a puff detection signal indicating whether or not a puff is currently occurring with respect to the nicotine e-vaping device; and a second PID controller configured such that, while the puff detection signal indicates that a puff is not currently occurring with respect to the nicotine e-vaping device, the second PID controller detects a change in an ambient temperature of the HWA, and the second PID controller controls the temperature setpoint such that the temperature setpoint changes in response to the detected change in the ambient temperature of the HWA.

The first PID controller may be configured to control the level of power applied by the nicotine e-vaping device to the HWA by generating a drive signal setting value, the level of power applied by the nicotine e-vaping device to the HWA being based on the drive signal setting value.

The second PID controller may be further configured to determine a flow rate of air flowing around the HWA based on the drive signal setting value, while the puff detection signal indicates that a puff is currently occurring with respect to the nicotine e-vaping device.

The puff detection signal generator is configured to determine a gradient of the drive signal setting value, and generate the puff detection signal based on the determined gradient of the drive signal setting value.

The nicotine e-vaping device may further include a drive signal generator configured to generate a pulse width modulated (PWM) drive signal based on the drive signal setting value, and apply the power to the HWA by applying the PWM drive signal to the HWA.

The drive signal generator may be configured to control a duty cycle of the PWM drive signal based on the drive signal setting value.

The first PID controller may be configured to generate the drive signal setting value based on a difference between the temperature of a heated element of the HWA and the temperature setpoint.

The second PID controller may be configured to detect the change in the ambient temperature of the HWA based on a difference between the drive signal setting value and a drive signal setting value setpoint.

The second PID controller may be configured to detect the change in the ambient temperature of the HWA based on a difference between the drive signal setting value and a drive signal setting value setpoint.

The second PID controller may be configured to control the temperature setpoint by increasing the temperature setpoint in response to detecting an increase in the ambient temperature of the HWA, and decreasing the temperature setpoint in response to detecting a decrease in the ambient temperature of the HWA.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
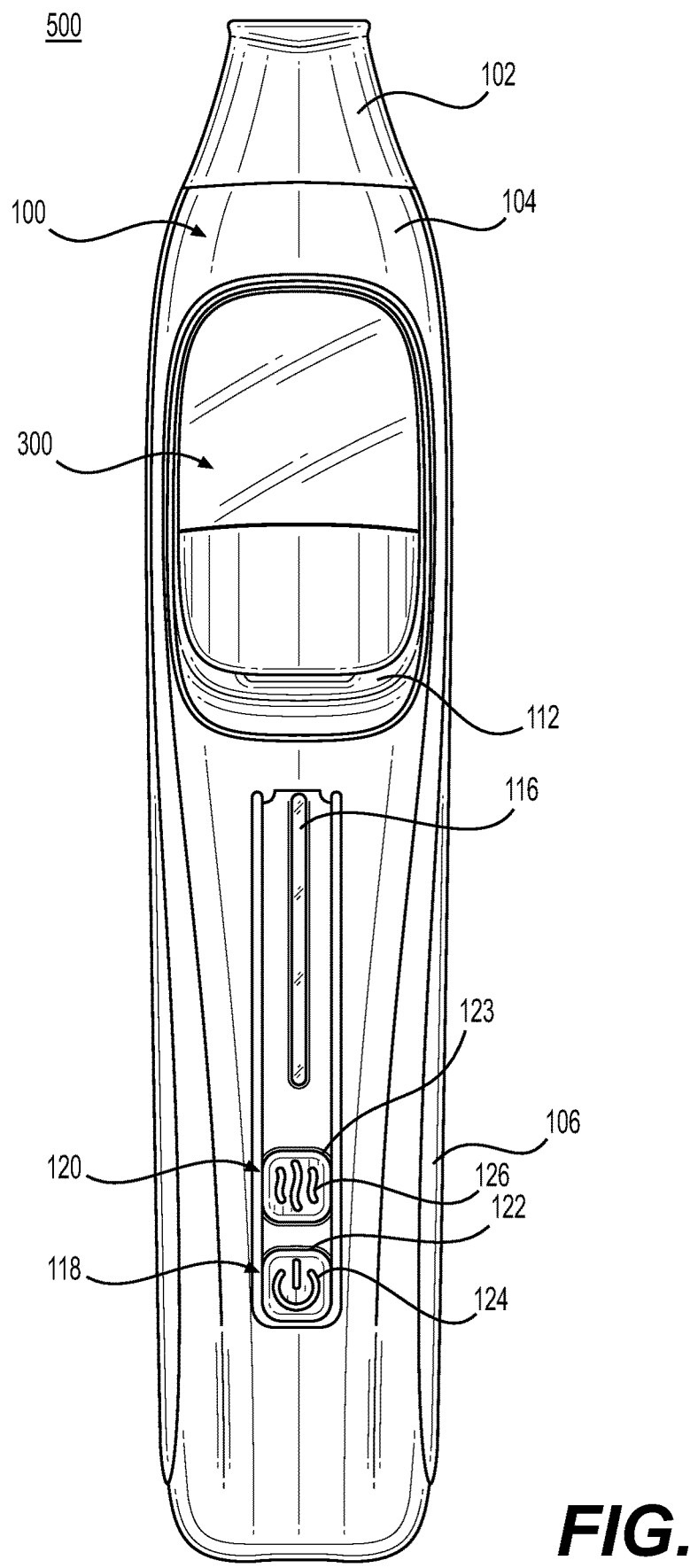
FIG. 1 is a front view of a nicotine e-vaping device according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example Nicotine E-Vapor Device Structure

A "nicotine e-vaping device" as used herein may be referred to on occasion using, and considered synonymous with, any of the terms: nicotine e-vapor device, nicotine e-vapor apparatus, and nicotine e-vaping apparatus.

Figure 2:
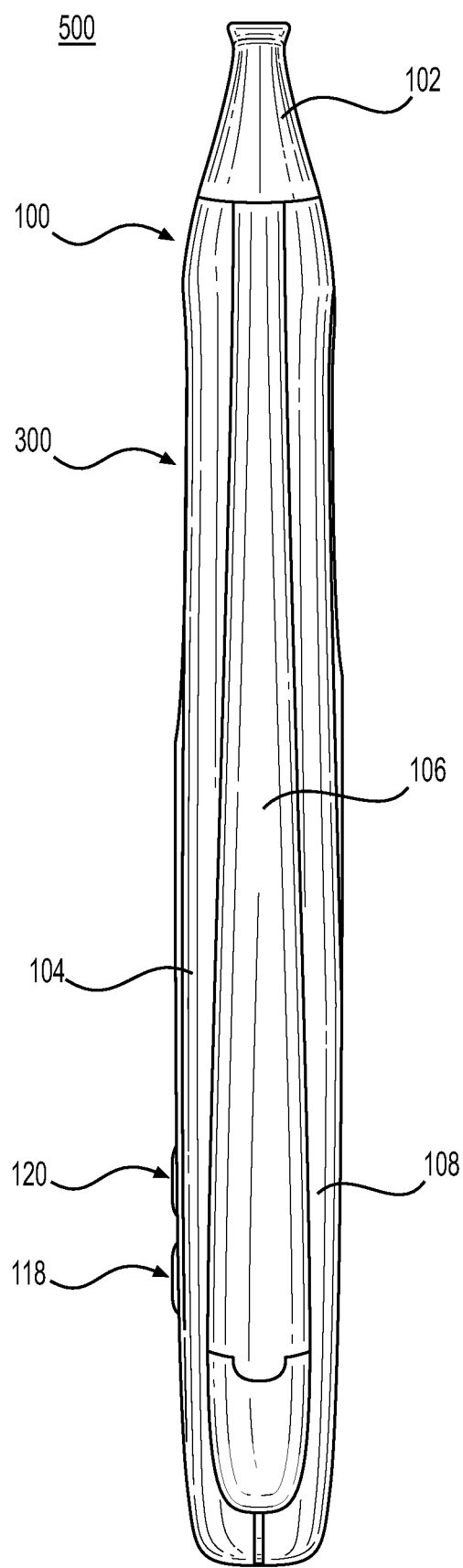
FIG. 2 is a side view of the nicotine e-vaping device of FIG. 1.
Figure 3:
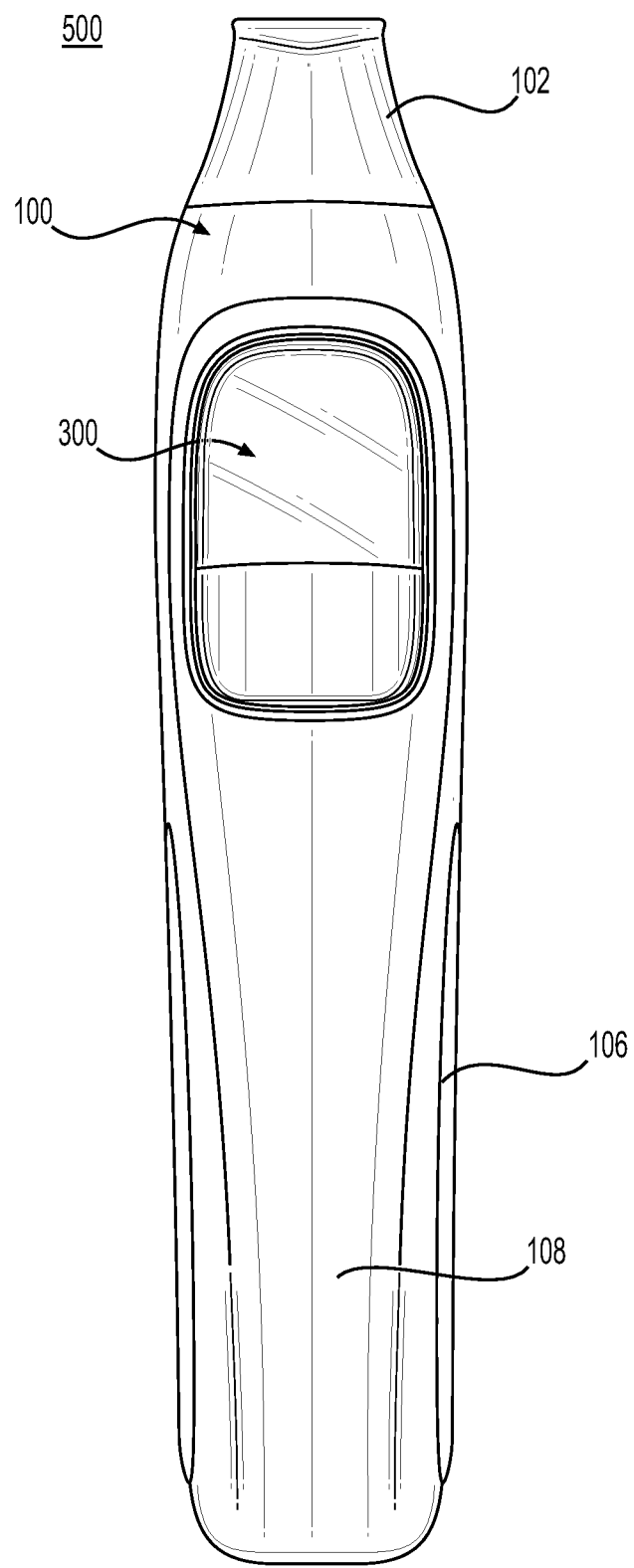
FIG. 3 is a rear view of the nicotine e-vaping device of FIG. 1.

FIG. 1 is a front view of a nicotine e-vaping device according to an example embodiment. FIG. 2 is a side view of the nicotine e-vaping device of FIG. 1. FIG. 3 is a rear view of the nicotine e-vaping device of FIG. 1. Referring to FIGS. 1-3, a nicotine e-vaping device 500 includes a device body 100 that is configured to receive a pod assembly 300. The pod assembly 300 is a modular article configured to hold a nicotine pre-vapor formulation. A "nicotine pre-vapor formulation" is a material or combination of materials that may be transformed into a nicotine vapor. For example, the nicotine pre-vapor formulation may be a liquid, solid, and/or gel formulation including, but not limited to, water, beads, solvents, active ingredients, ethanol, plant extracts, natural or artificial flavors, and/or vapor formers such as glycerin and propylene glycol. During vaping, the nicotine e-vaping device 500 is configured to heat the nicotine pre-vapor formulation to generate a nicotine vapor. As referred to herein, a "vapor" is any matter generated or outputted from any nicotine e-vaping device according to any of the example embodiments disclosed herein.

The device body 100 includes a front cover 104, a frame 106, and a rear cover 108. The front cover 104, the frame 106, and the rear cover 108 form a device housing that encloses mechanical components, electronic components, and/or circuitry associated with the operation of the nicotine e-vaping device 500. For instance, the device housing of the device body 100 may enclose a power source configured to power the nicotine e-vaping device 500, which may include supplying an electric current to the pod assembly 300. In addition, when assembled, the front cover 104, the frame 106, and the rear cover 108 may constitute a majority of the visible portion of the device body 100.

The front cover 104 (e.g., first cover) defines a primary opening configured to accommodate a bezel structure 112. The bezel structure 112 defines a through hole 150 configured to receive the pod assembly 300. The through hole 150 is discussed herein in more detail in connection with, for instance, FIG. 9.

The front cover 104 also defines a secondary opening configured to accommodate a light guide arrangement. The secondary opening may resemble a slot (e.g., segmented slot), although other shapes are possible depending on the shape of the light guide arrangement. In an example embodiment, the light guide arrangement includes a light guide lens 116. Furthermore, the front cover 104 defines a tertiary opening and a quaternary opening configured to accommodate a first button 118 and a second button 120. Each of the tertiary opening and the quaternary opening may resemble a rounded square, although other shapes are possible depending on the shapes of the buttons. A first button housing 122 is configured to expose a first button lens 124, while a second button housing 123 is configured to expose a second button lens 126.

The operation of the nicotine e-vaping device 500 may be controlled by the first button 118 and the second button 120. For instance, the first button 118 may be a power button, and the second button 120 may be an intensity button. Although two buttons are shown in the drawings in connection with the light guide arrangement, it should be understood that more (or less) buttons may be provided depending on the available features and desired user interface.

The frame 106 (e.g., base frame) is the central support structure for the device body 100 (and the nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, "proximal" (and, conversely, "distal") is in relation to an adult vaper during vaping, and "downstream" (and, conversely, "upstream") is in relation to a flow of the nicotine vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the nicotine e-vaping device 500.

The rear cover 108 (e.g., second cover) also defines an opening configured to accommodate the bezel structure 112. The front cover 104 and the rear cover 108 may be configured to engage with the frame 106 via a snap-fit arrangement.

The device body 100 also includes a mouthpiece 102. The mouthpiece 102 may be secured to the proximal end of the frame 106.

Figure 4:
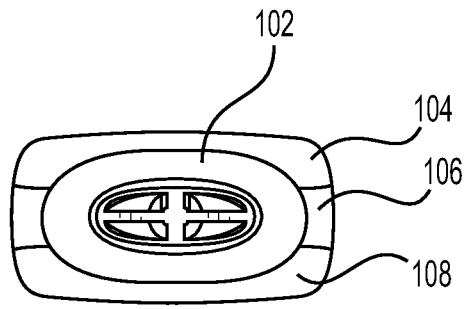
FIG. 4 is a proximal end view of the nicotine e-vaping device of FIG. 1.

FIG. 4 is a proximal end view of the nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped.

Figure 5:
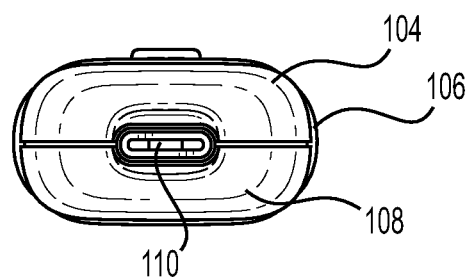
FIG. 5 is a distal end view of the nicotine e-vaping device of FIG. 1.

FIG. 5 is a distal end view of the nicotine e-vaping device of FIG. 1. Referring to FIG. 5, the distal end of the nicotine e-vaping device 500 includes a port 110. The port 110 is configured to receive an electric current (e.g., via a USB cable) from an external power source so as to charge an internal power source within the nicotine e-vaping device 500. In addition, the port 110 may also be configured to send data to and/or receive data (e.g., via a USB cable) from another nicotine e-vaping device or other electronic device (e.g., phone, tablet, computer). Furthermore, the nicotine e-vaping device 500 may be configured for wireless communication with another electronic device, such as a phone, via an application software (app) installed on that electronic device. In such an instance, an adult vaper may control or otherwise interface with the nicotine e-vaping device 500 (e.g., locate the nicotine e-vaping device 500, check usage information, change operating parameters) through the app.

Figure 6:
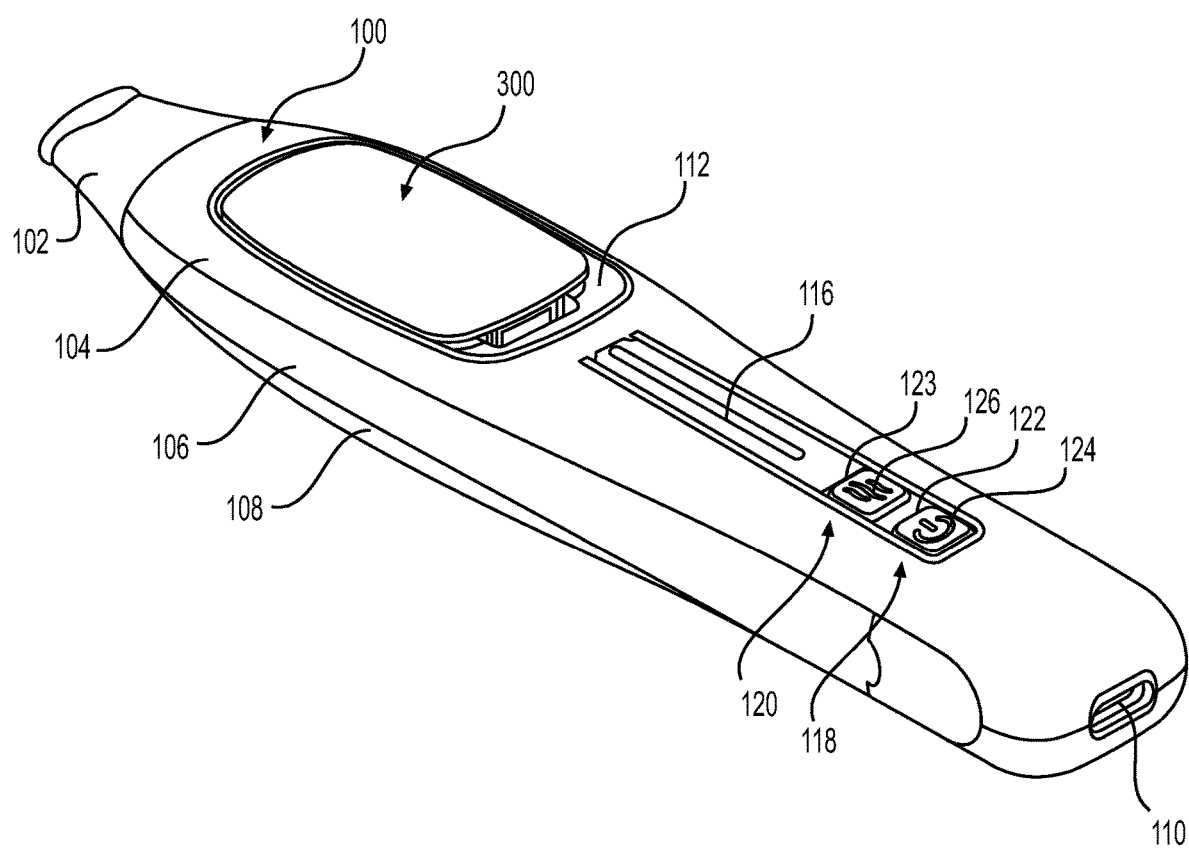
FIG. 6 is a perspective view of the nicotine e-vaping device of FIG. 1.
Figure 7:
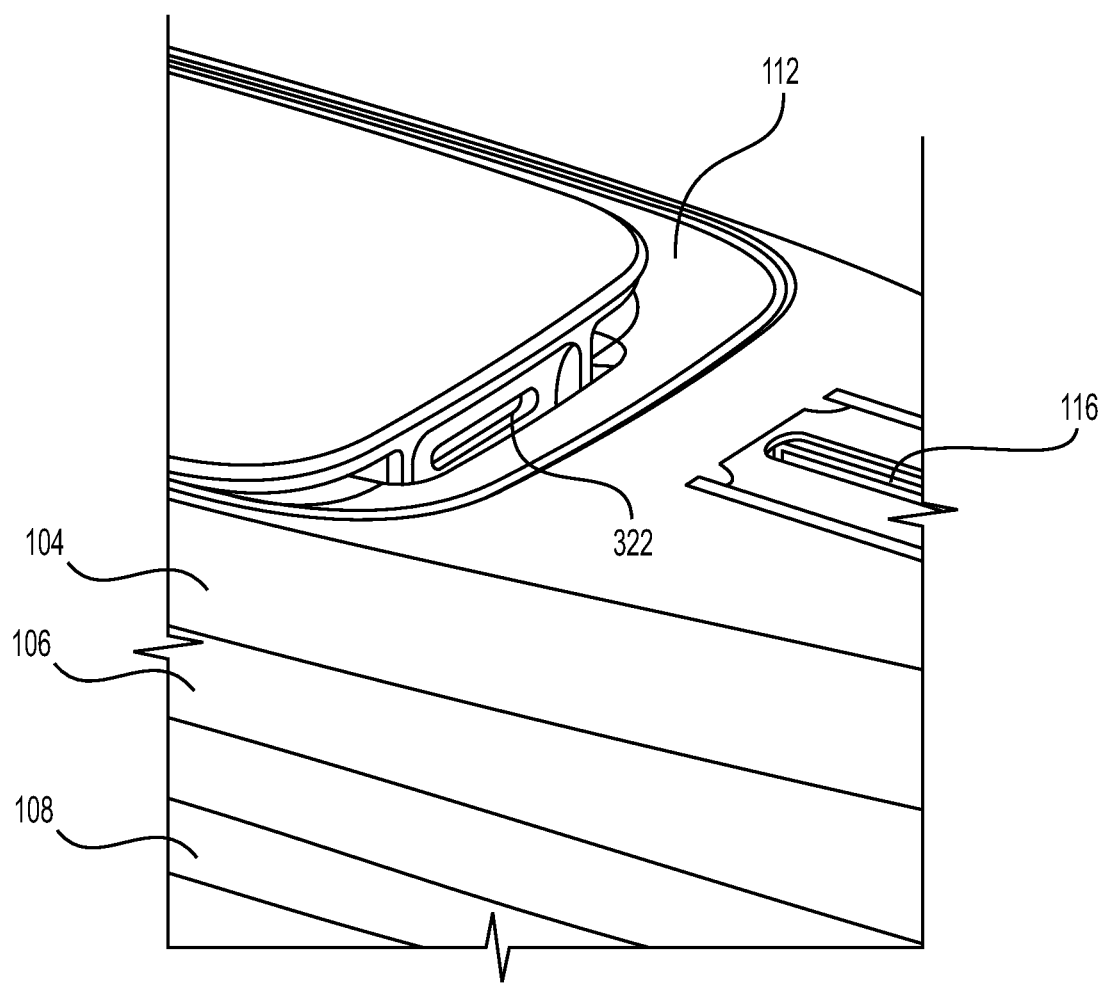
FIG. 7 is an enlarged view of the pod inlet in FIG. 6.

FIG. 6 is a perspective view of the nicotine e-vaping device of FIG. 1. FIG. 7 is an enlarged view of the pod inlet in FIG. 6. Referring to FIGS. 6-7, and as briefly noted above, the nicotine e-vaping device 500 includes a pod assembly 300 configured to hold a nicotine pre-vapor formulation. The pod assembly 300 has an upstream end (which faces the light guide arrangement) and a downstream end (which faces the mouthpiece 102). In a non-limiting embodiment, the upstream end is an opposing surface of the pod assembly 300 from the downstream end. The upstream end of the pod assembly 300 defines a pod inlet 322. The device body 100 defines a through hole (e.g., through hole 150 in FIG. 9) configured to receive the pod assembly 300. In an example embodiment, the bezel structure 112 of the device body 100 defines the through hole and includes an upstream rim. As shown, particularly in FIG. 7, the upstream rim of the bezel structure 112 is angled (e.g., dips inward) so as to expose the pod inlet 322 when the pod assembly 300 is seated within the through hole of the device body 100.

For instance, rather than following the contour of the front cover 104 (so as to be relatively flush with the front face of the pod assembly 300 and, thus, obscure the pod inlet 322), the upstream rim of the bezel structure 112 is in a form of a scoop configured to direct ambient air into the pod inlet 322. This angled/scoop configuration may help reduce or prevent the blockage of the air inlet (e.g., pod inlet 322) of the nicotine e-vaping device 500. The depth of the scoop may be such that less than half (e.g., less than a quarter) of the upstream end face of the pod assembly 300 is exposed. Additionally, in a non-limiting embodiment, the pod inlet 322 is in a form of a slot. Furthermore, if the device body 100 is regarded as extending in a first direction, then the slot may be regarded as extending in a second direction, wherein the second direction is transverse to the first direction.

Figure 8:
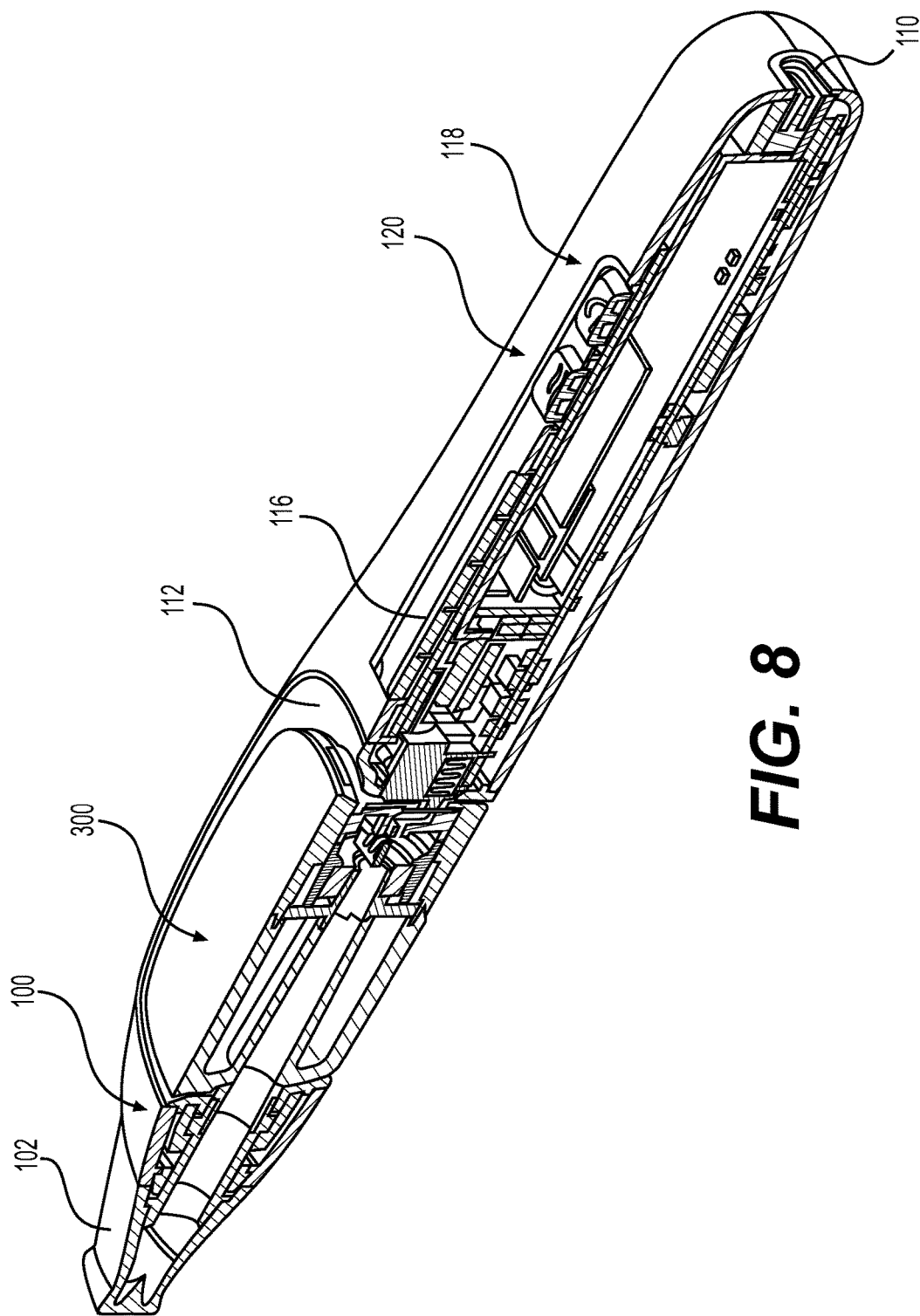
FIG. 8 is a cross-sectional view of the nicotine e-vaping device of FIG. 6.

FIG. 8 is a cross-sectional view of the nicotine e-vaping device of FIG. 6. In FIG. 8, the cross-section is taken along the longitudinal axis of the nicotine e-vaping device 500. As shown, the device body 100 and the pod assembly 300 include mechanical components, electronic components, and/or circuitry associated with the operation of the nicotine e-vaping device 500, which are discussed in more detail herein and/or are incorporated by reference herein. For instance, the pod assembly 300 may include mechanical components configured to actuate to release the nicotine pre-vapor formulation from a sealed reservoir within. The pod assembly 300 may also have mechanical aspects configured to engage with the device body 100 to facilitate the insertion and seating of the pod assembly 300.

Additionally, the pod assembly 300 may be a "smart pod" that includes electronic components and/or circuitry configured to store, receive, and/or transmit information to/from the device body 100. Such information may be used to authenticate the pod assembly 300 for use with the device body 100 (e.g., to prevent usage of an unapproved/counterfeit pod assembly). Furthermore, the information may be used to identify a type of the pod assembly 300 which is then correlated with a vaping profile based on the identified type. The vaping profile may be designed to set forth the general parameters for the heating of the nicotine pre-vapor formulation and may be subject to tuning, refining, or other adjustment by an adult vaper before and/or during vaping.

The pod assembly 300 may also communicate with the device body 100 other information that may be relevant to the operation of the nicotine e-vaping device 500. Examples of relevant information may include a level of the nicotine pre-vapor formulation within the pod assembly 300 and/or a length of time that has passed since the pod assembly 300 was inserted into the device body 100 and activated.

The device body 100 may include mechanical components (e.g. complementary structures) configured to engage, hold, and/or activate the pod assembly 300. In addition, the device body 100 may include electronic components and/or circuitry configured to receive an electric current to charge an internal power source (e.g., battery) which, in turn, is configured to supply power to the pod assembly 300 during vaping. Furthermore, the device body 100 may include electronic components and/or circuitry configured to communicate with the pod assembly 300, a different nicotine e-vaping device, other electronic devices (e.g., phone, tablet, computer), and/or the adult vaper.

Figure 9:
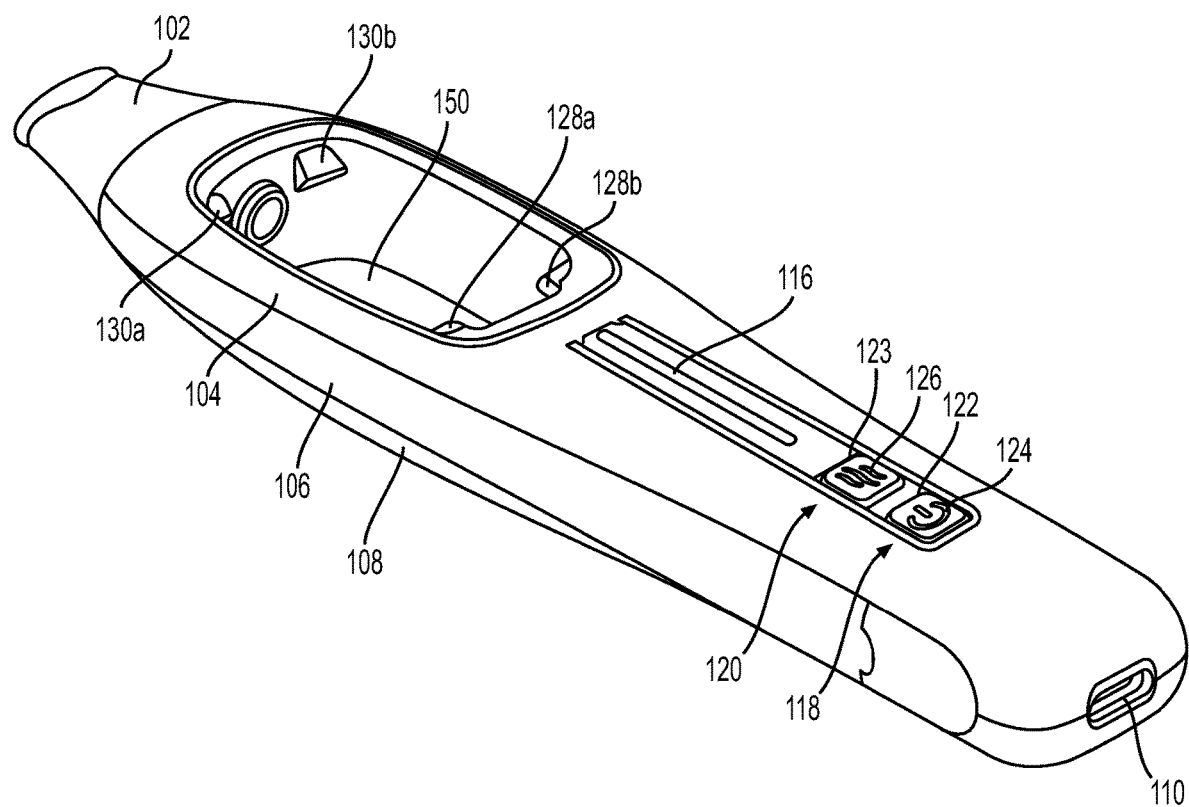
FIG. 9 is a perspective view of the device body of the nicotine e-vaping device of FIG. 6.

FIG. 9 is a perspective view of the device body of the nicotine e-vaping device of FIG. 6. Referring to FIG. 9, the bezel structure 112 of the device body 100 defines a through hole 150. The through hole 150 is configured to receive a pod assembly 300. To facilitate the insertion and seating of the pod assembly 300 within the through hole 150, the upstream rim of the bezel structure 112 includes a first upstream protrusion 128a and a second upstream protrusion 128b.

The downstream sidewall of the bezel structure 112 may define a first downstream opening, a second downstream opening, and a third downstream opening. A retention structure including a first downstream protrusion 130a and a second downstream protrusion 130b is engaged with the bezel structure 112 such that the first downstream protrusion 130a and the second downstream protrusion 130b protrude through the first downstream opening and the second downstream opening, respectively, of the bezel structure 112 and into the through hole 150.

Figure 10:
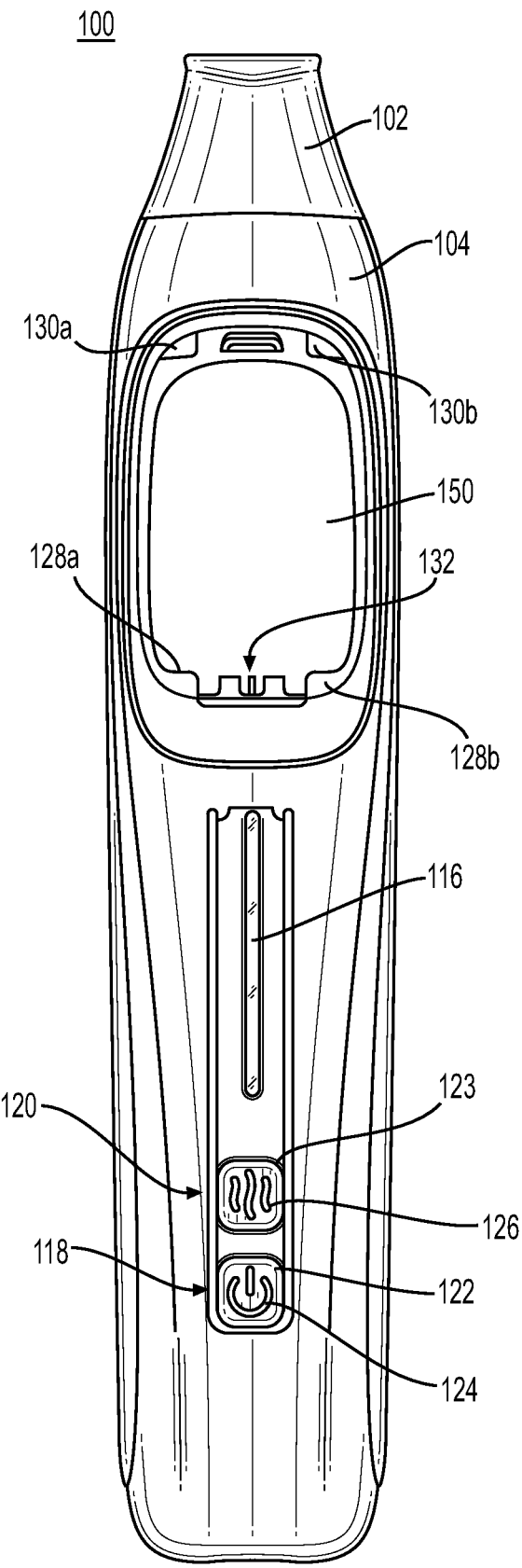
FIG. 10 is a front view of the device body of FIG. 9.

FIG. 10 is a front view of the device body of FIG. 9. Referring to FIG. 10, the device body 100 includes a device electrical connector 132 disposed at an upstream side of the through hole 150. The device electrical connector 132 of the device body 100 is configured to electrically engage with a pod assembly 300 that is seated within the through hole 150. As a result, power can be supplied from the device body 100 to the pod assembly 300 via the device electrical connector 132 during vaping. In addition, data can be sent to and/or received from the device body 100 and the pod assembly 300 via the device electrical connector 132.

Figure 11:
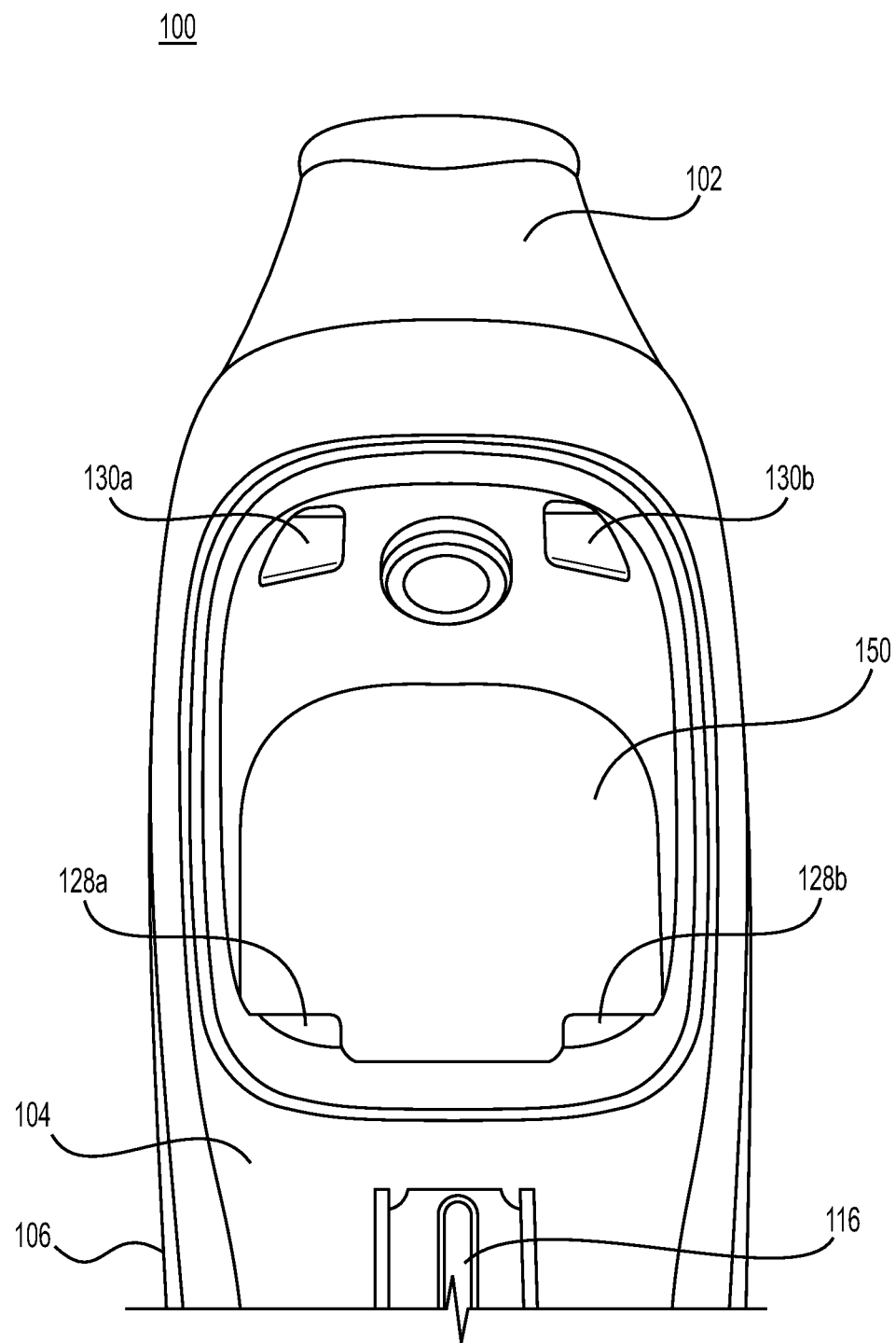
FIG. 11 is an enlarged perspective view of the through hole in FIG. 10.

FIG. 11 is an enlarged perspective view of the through hole in FIG. 10. Referring to FIG. 11, the first upstream protrusion 128a, the second upstream protrusion 128b, the first downstream protrusion 130a, the second downstream protrusion 130b, and the distal end of the mouthpiece 102 protrude into the through hole 150. In an example embodiment, the first upstream protrusion 128a and the second upstream protrusion 128b are stationary structures (e.g., stationary pivots), while the first downstream protrusion 130a and the second downstream protrusion 130b are tractable structures (e.g., retractable members). For instance, the first downstream protrusion 130a and the second downstream protrusion 130b may be configured (e.g., springloaded) to default to a protracted state while also configured to transition temporarily to a retracted state (and reversibly back to the protracted state) to facilitate an insertion of a pod assembly 300.

Figure 12:
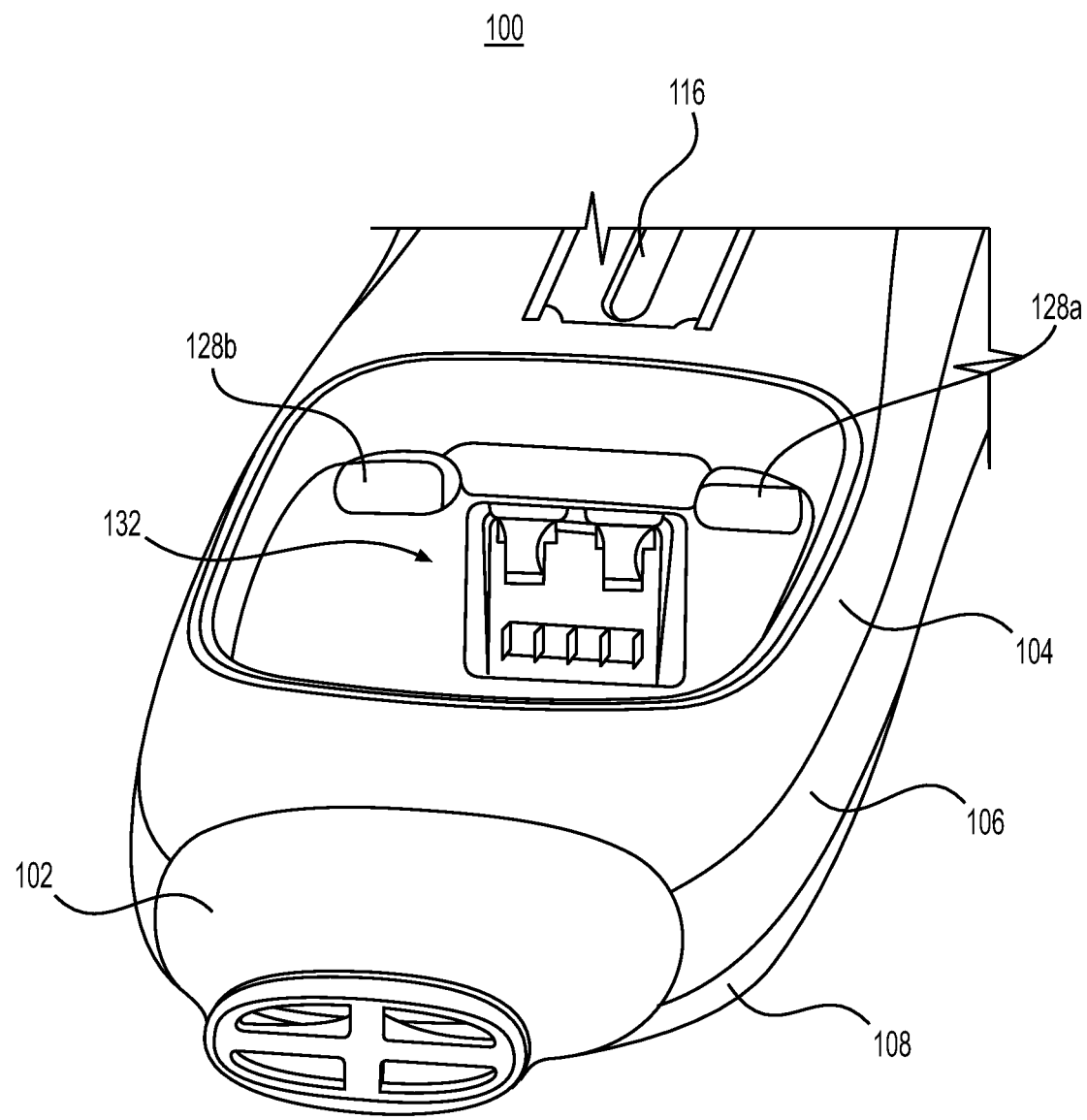
FIG. 12 is an enlarged perspective view of the device electrical connector in FIG. 10.

FIG. 12 is an enlarged perspective view of the device electrical contacts in FIG. 10. The device electrical contacts of the device body 100 are configured to engage with the pod electrical contacts of the pod assembly 300 when the pod assembly 300 is seated within the through hole 150 of the device body 100. Referring to FIG. 12, the device electrical contacts of the device body 100 include the device electrical connector 132. The device electrical connector 132 includes power contacts and data contacts. The power contacts of the device electrical connector 132 are configured to supply power from the device body 100 to the pod assembly 300. As illustrated, the power contacts of the device electrical connector 132 include a first pair of power contacts and a second pair of power contacts (which are positioned so as to be closer to the front cover 104 than the rear cover 108). The first pair of power contacts (e.g., the pair adjacent to the first upstream protrusion 128a) may be a single integral structure that is distinct from the second pair of power contacts and that, when assembled, includes two projections that extend into the through hole 150. Similarly, the second pair of power contacts (e.g., the pair adjacent to the second upstream protrusion 128b) may be a single integral structure that is distinct from the first pair of power contacts and that, when assembled, includes two projections that extend into the through hole 150. The first pair of power contacts and the second pair of power contacts of the device electrical connector 132 may be tractably-mounted and biased so as to protract into the through hole 150 as a default and to retract (e.g., independently) from the through hole 150 when subjected to a force that overcomes the bias.

Figure 13:
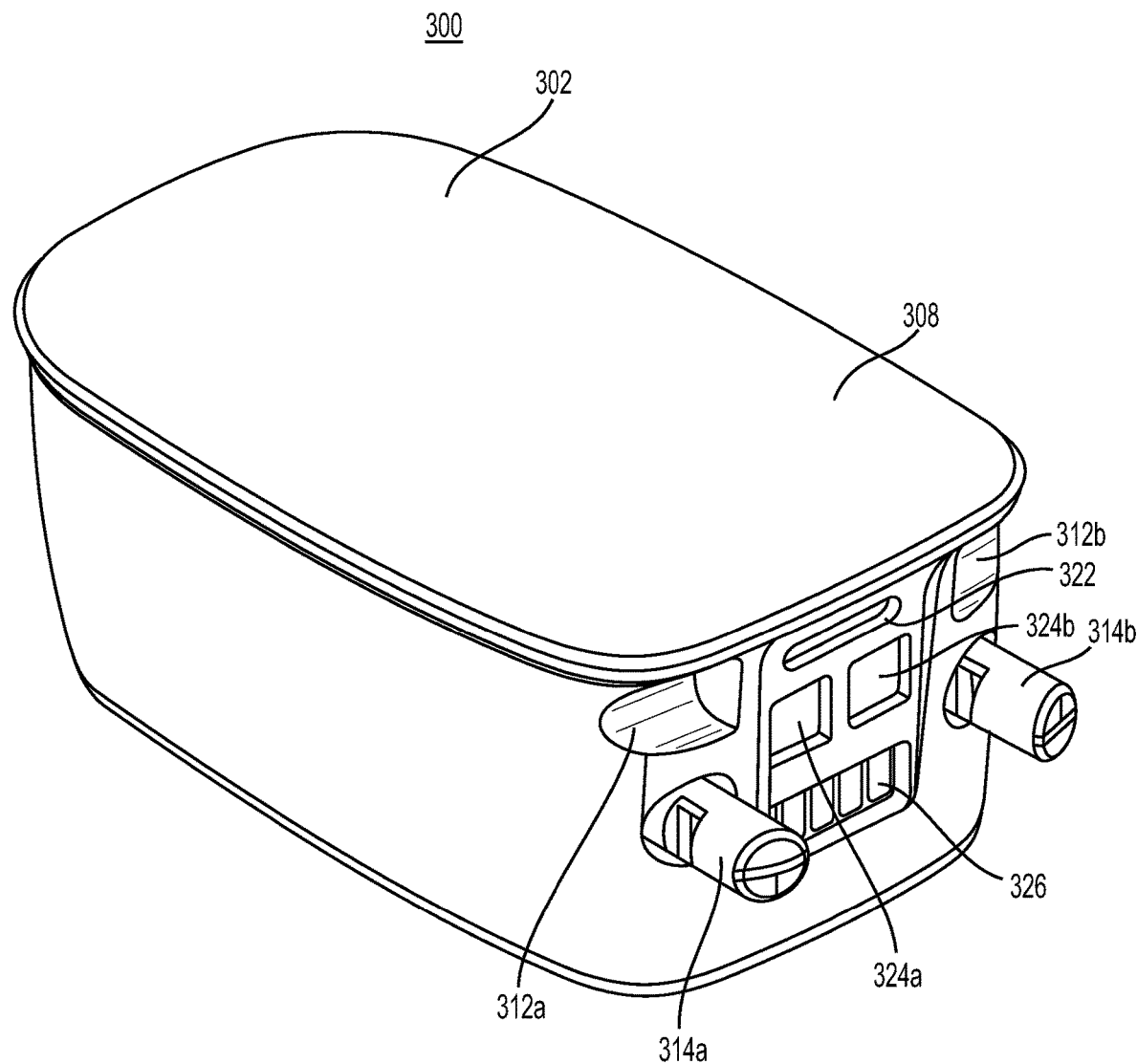
FIG. 13 is a perspective view of the pod assembly of the nicotine e-vaping device in FIG. 6.
Figure 14:
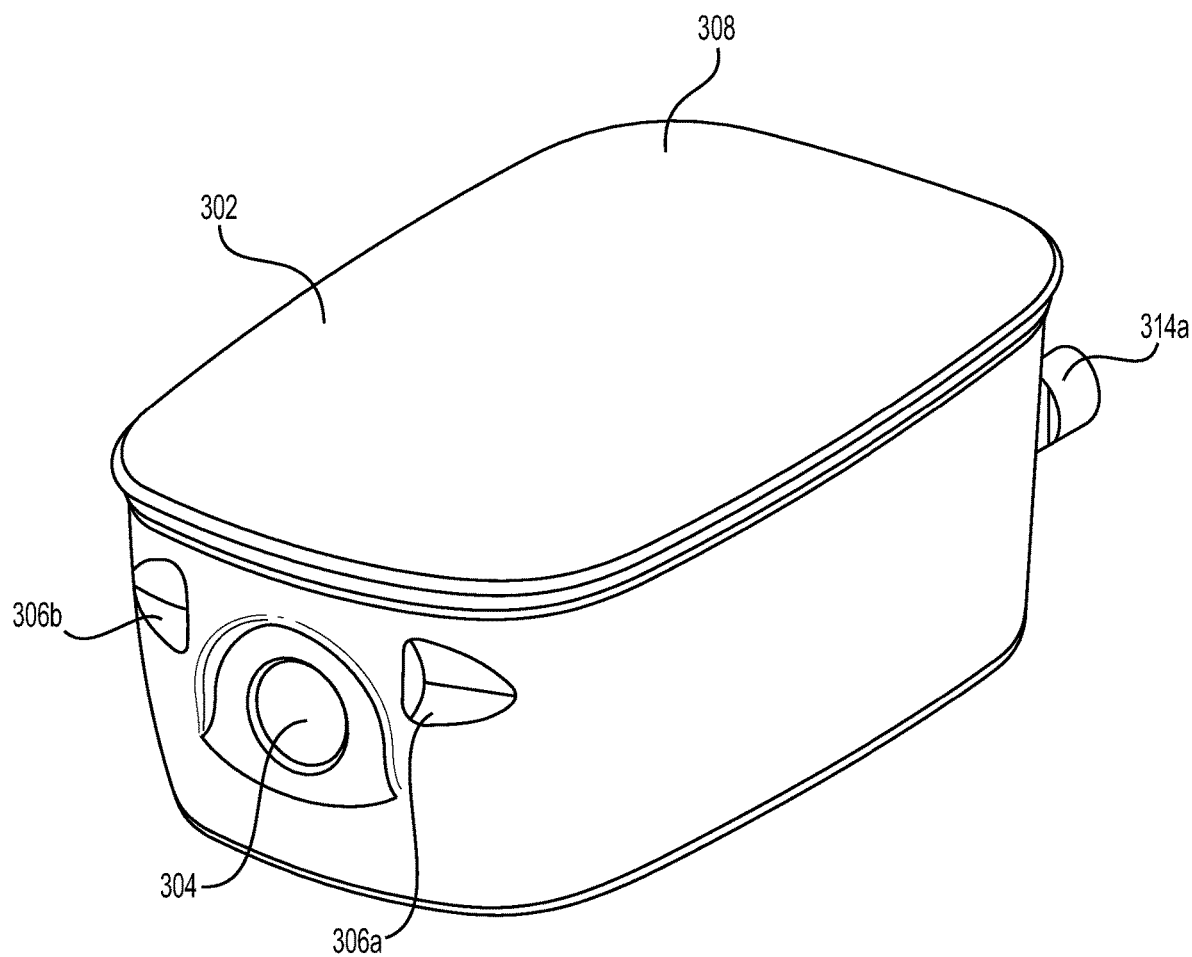
FIG. 14 is another perspective view of the pod assembly of FIG. 13.

FIG. 13 is a perspective view of the pod assembly of the nicotine e-vaping device in FIG. 6. FIG. 14 is another perspective view of the pod assembly of FIG. 13.

FIG. 13 is a perspective view of the pod assembly of the nicotine e-vaping device in FIG. 6. FIG. 14 is another perspective view of the pod assembly of FIG. 13. Referring to FIGS. 13 and 14, the pod assembly 300 for the nicotine e-vaping device 500 includes a pod body configured to hold a nicotine pre-vapor formulation. Thus, the pod assembly 300 is an example of a nicotine pre-vapor formulation storage portion of the nicotine e-vaping device 500. The pod body has an upstream end and a downstream end. The upstream end of the pod body defines a pod inlet 322. The downstream end of the pod body defines a pod outlet 304 that is in fluidic communication with the pod inlet 322 at the upstream end. During vaping, air enters the pod assembly 300 via the pod inlet 322, and vapor exits the pod assembly 300 via the pod outlet 304. The pod inlet 322 is shown in the drawings as being in a form of a slot. However, it should be understood that example embodiments are not limited thereto and that other forms are possible.

The pod assembly 300 includes a connector module 320 (e.g., FIG. 16) that is disposed within the pod body and exposed by openings in the upstream end. The external face of the connector module 320 includes at least one electrical contact. The at least one electrical contact may include a plurality of power contacts. For instance, the plurality of power contacts may include a first power contact 324a and a second power contact 324b. The first power contact 324a of the pod assembly 300 is configured to electrically connect with the first power contact (e.g., the power contact adjacent to the first upstream protrusion 128a in FIG. 12) of the device electrical connector 132 of the device body 100. Similarly, the second power contact 324b of the pod assembly 300 is configured to electrically connect with the second power contact (e.g., the power contact adjacent to the second upstream protrusion 128b in FIG. 12) of the device electrical connector 132 of the device body 100. In addition, the at least one electrical contact of the pod assembly 300 includes a plurality of data contacts 326. The plurality of data contacts 326 of the pod assembly 300 are configured to electrically connect with the data contacts of the device electrical connector 132 (e.g., row of five projections in FIG. 12). While two power contacts and five data contacts are shown in connection with the pod assembly 300, it should be understood that other variations are possible depending on the design of the device body 100.

In an example embodiment, the pod assembly 300 includes a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The external face of the connector module 320 (that is exposed by the pod body) may be regarded as being part of the upstream end face of the pod assembly 300. The front face of the pod assembly 300 may be wider and longer than the rear face. In such an instance, the first side face and the second side face may be angled inwards towards each other. The upstream end face and the downstream end face may also be angled inwards towards each other. Because of the angled faces, the insertion of the pod assembly 300 will be unidirectional (e.g., from the front side (side associated with the front cover 104) of the device body 100). As a result, the possibility that the pod assembly 300 will be improperly inserted into the device body 100 can be reduced or prevented.

As illustrated, the pod body of the pod assembly 300 includes a first housing section 302 and a second housing section 308. The first housing section 302 has a downstream end defining the pod outlet 304. The rim of the pod outlet 304 may optionally be a sunken or indented region. In such an instance, this region may resemble a cove, wherein the side of the rim adjacent to the rear face of the pod assembly 300 may be open, while the side of the rim adjacent to the front face may be surrounded by a raised portion of the downstream end of the first housing section 302. The raised portion may function as a stopper for the distal end of the mouthpiece 102. As a result, this configuration for the pod outlet 304 may facilitate the receiving and aligning of the distal end of the mouthpiece 102 (e.g., FIG. 11) via the open side of the rim and its subsequent seating against the raised portion of the downstream end of the first housing section 302. In a non-limiting embodiment, the distal end of the mouthpiece 102 may also include (or be formed of) a resilient material to help create a seal around the pod outlet 304 when the pod assembly 300 is properly inserted within the through hole 150 of the device body 100.

The downstream end of the first housing section 302 additionally defines at least one downstream recess. In an example embodiment, the at least one downstream recess is in a form of a first downstream recess 306a and a second downstream recess 306b. The pod outlet 304 may be between the first downstream recess 306a and the second downstream recess 306b. The first downstream recess 306a and the second downstream recess 306b are configured to engage with the first downstream protrusion 130a and the second downstream protrusion 130b, respectively, of the device body 100. As shown in FIG. 11, the first downstream protrusion 130a and the second downstream protrusion 130b of the device body 100 may be disposed on adjacent corners of the downstream sidewall of the through hole 150. The first downstream recess 306a and the second downstream recess 306b may each be in a form of a V-shaped notch. In such an instance, each of the first downstream protrusion 130a and the second downstream protrusion 130b of the device body 100 may be in a form of a wedge-shaped structure configured to engage with a corresponding V-shaped notch of the first downstream recess 306a and the second downstream recess 306b. The first downstream recess 306a may abut the corner of the downstream end face and the first side face, while the second downstream recess 306b may abut the corner of the downstream end face and the second side face. As a result, the edges of the first downstream recess 306a and the second downstream recess 306b adjacent to the first side face and the second side face, respectively, may be open. In such an instance, as shown in FIG. 14, each of the first downstream recess 306a and the second downstream recess 306b may be a 3-sided recess.

The second housing section 308 has an upstream end further defining (in addition to the pod inlet 322) a plurality of openings (e.g., first power contact opening 325a, second power contact opening 325b, data contact opening 327) configured to expose the connector module 320 (FIGS. 15-16) within the pod assembly 300. The upstream end of the second housing section 308 also defines at least one upstream recess. In an example embodiment, the at least one upstream recess is in a form of a first upstream recess 312a and a second upstream recess 312b. The pod inlet 322 may be between the first upstream recess 312a and the second upstream recess 312b. The first upstream recess 312a and the second upstream recess 312b are configured to engage with the first upstream protrusion 128a and the second upstream protrusion 128b, respectively, of the device body 100. As shown in FIG. 12, the first upstream protrusion 128a and the second upstream protrusion 128b of the device body 100 may be disposed on adjacent corners of the upstream sidewall of the through hole 150. A depth of each of the first upstream recess 312a and the second upstream recess 312b may be greater than a depth of each of the first downstream recess 306a and the second downstream recess 306b. A terminus of each of the first upstream recess 312a and the second upstream recess 312b may also be more rounded than a terminus of each of the first downstream recess 306a and the second downstream recess 306b. For instance, the first upstream recess 312a and the second upstream recess 312b may each be in a form of a U-shaped indentation. In such an instance, each of the first upstream protrusion 128a and the second upstream protrusion 128b of the device body 100 may be in a form of a rounded knob configured to engage with a corresponding U-shaped indentation of the first upstream recess 312a and the second upstream recess 312b. The first upstream recess 312a may abut the corner of the upstream end face and the first side face, while the second upstream recess 312b may abut the corner of the upstream end face and the second side face. As a result, the edges of the first upstream recess 312a and the second upstream recess 312b adjacent to the first side face and the second side face, respectively, may be open.

The first housing section 302 may define a reservoir within configured to hold the nicotine pre-vapor formulation. The reservoir may be configured to hermetically seal the nicotine pre-vapor formulation until an activation of the pod assembly 300 to release the nicotine pre-vapor formulation from the reservoir. As a result of the hermetic seal, the nicotine pre-vapor formulation may be isolated from the environment as well as the internal elements of the pod assembly 300 that may potentially react with the nicotine pre-vapor formulation, thereby reducing or preventing the possibility of adverse effects to the shelf-life and/or sensorial characteristics (e.g., flavor) of the nicotine pre-vapor formulation. The second housing section 308 may contain structures configured to activate the pod assembly 300 and to receive and heat the nicotine pre-vapor formulation released from the reservoir after the activation.

The pod assembly 300 may be activated manually by an adult vaper prior to the insertion of the pod assembly 300 into the device body 100. Alternatively, the pod assembly 300 may be activated as part of the insertion of the pod assembly 300 into the device body 100. In an example embodiment, the second housing section 308 of the pod body includes a perforator configured to release the nicotine pre-vapor formulation from the reservoir in the first housing section 302 during the activation of the pod assembly 300. The perforator may be in a form of a first activation pin 314a and a second activation pin 314b, which will be discussed in more detail herein.

To activate the pod assembly 300 manually, an adult vaper may press the first activation pin 314a and the second activation pin 314b inward (e.g., simultaneously or sequentially) prior to inserting the pod assembly 300 into the through hole 150 of the device body 100. For instance, the first activation pin 314a and the second activation pin 314b may be manually pressed until the ends thereof are substantially even with the upstream end face of the pod assembly 300. In an example embodiment, the inward movement of the first activation pin 314a and the second activation pin 314b causes a seal of the reservoir to be punctured or otherwise compromised so as to release the nicotine pre-vapor formulation therefrom.

Alternatively, to activate the pod assembly 300 as part of the insertion of the pod assembly 300 into the device body 100, the pod assembly 300 is initially positioned such that the first upstream recess 312a and the second upstream recess 312b are engaged with the first upstream protrusion 128a and the second upstream protrusion 128b, respectively (e.g., upstream engagement). Because each of the first upstream protrusion 128a and the second upstream protrusion 128b of the device body 100 may be in a form of a rounded knob configured to engage with a corresponding U-shaped indentation of the first upstream recess 312a and the second upstream recess 312b, the pod assembly 300 may be subsequently pivoted with relative ease about the first upstream protrusion 128a and the second upstream protrusion 128b and into the through hole 150 of the device body 100.

With regard to the pivoting of the pod assembly 300, the axis of rotation may be regarded as extending through the first upstream protrusion 128a and the second upstream protrusion 128b and oriented orthogonally to a longitudinal axis of the device body 100. During the initial positioning and subsequent pivoting of the pod assembly 300, the first activation pin 314a and the second activation pin 314b will come into contact with the upstream sidewall of the through hole 150 and transition from a protracted state to a retracted state as the first activation pin 314a and the second activation pin 314b are pushed (e.g., simultaneously) into the second housing section 308 as the pod assembly 300 progresses into the through hole 150. When the downstream end of the pod assembly 300 reaches the vicinity of the downstream sidewall of the through hole 150 and comes into contact with the first downstream protrusion 130a and the second downstream protrusion 130b, the first downstream protrusion 130a and the second downstream protrusion 130b will retract and then resiliently protract (e.g., spring back) when the positioning of the pod assembly 300 allows the first downstream protrusion 130a and the second downstream protrusion 130b of the device body 100 to engage with the first downstream recess 306a and the second downstream recess 306b, respectively, of the pod assembly 300 (e.g., downstream engagement).

As noted supra, according to an example embodiment, the mouthpiece 102 is secured to the retention structure 140 (of which the first downstream protrusion 130a and the second downstream protrusion 130b are a part). In such an instance, the retraction of the first downstream protrusion 130a and the second downstream protrusion 130b from the through hole 150 will cause a simultaneous shift of the mouthpiece 102 by a corresponding distance in the same direction (e.g., downstream direction). Conversely, the mouthpiece 102 will spring back simultaneously with the first downstream protrusion 130a and the second downstream protrusion 130b when the pod assembly 300 has been sufficiently inserted to facilitate downstream engagement. In addition to the resilient engagement by the first downstream protrusion 130a and the second downstream protrusion 130b, the distal end of the mouthpiece 102 is configured to also be biased against the pod assembly 300 (and aligned with the pod outlet 304 so as to form a relatively vapor-tight seal) when the pod assembly 300 is properly seated within the through hole 150 of the device body 100.

Furthermore, the downstream engagement may produce an audible click and/or a haptic feedback to indicate that the pod assembly 300 is properly seated within the through hole 150 of the device body 100. When properly seated, the pod assembly 300 will be connected to the device body 100 mechanically, electrically, and fluidically. Although the non-limiting embodiments herein describe the upstream engagement of the pod assembly 300 as occurring before the downstream engagement, it should be understood that the pertinent mating, activation, and/or electrical arrangements may be reversed such that the downstream engagement occurs before the upstream engagement.

Figure 15:
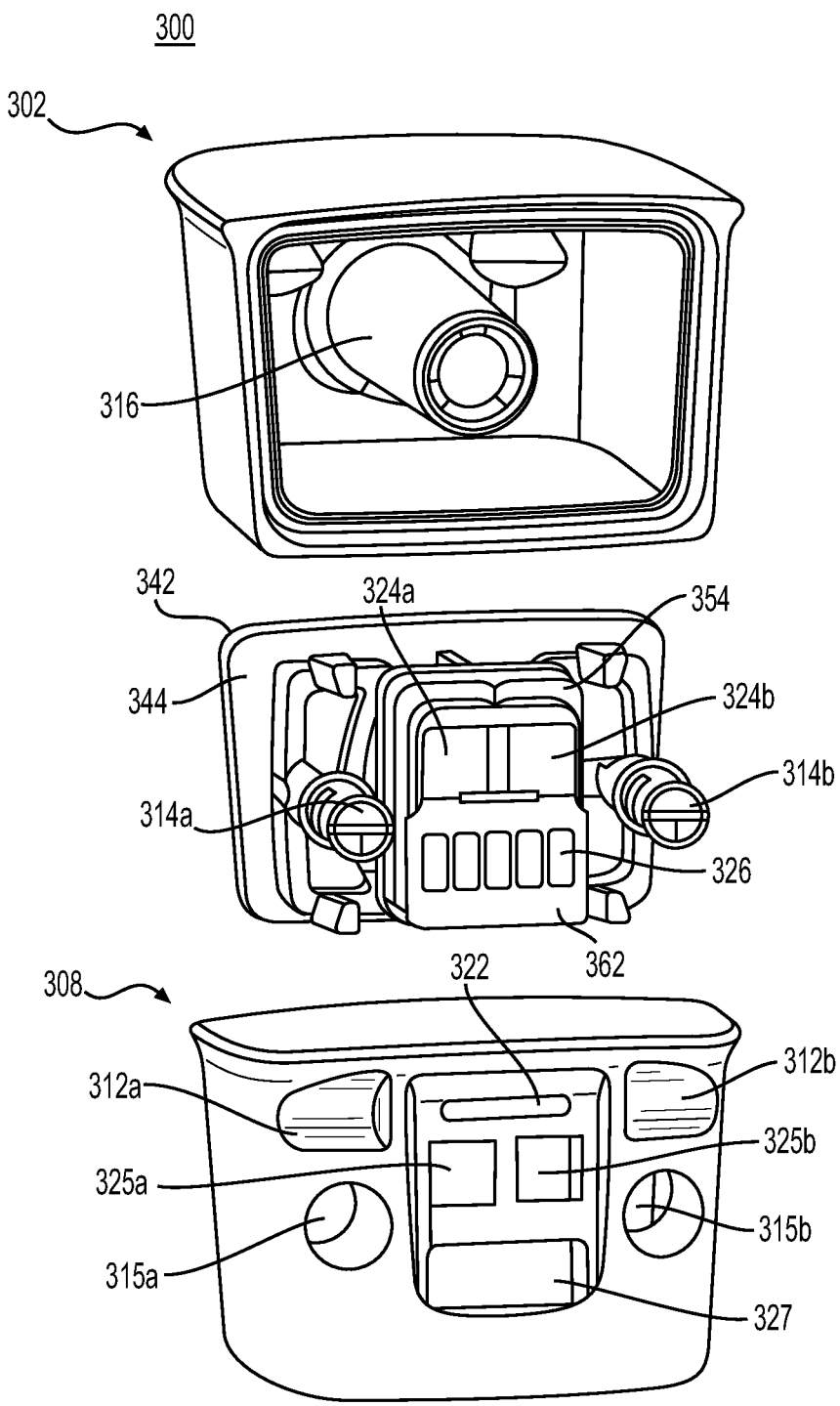
FIG. 15 is a partially exploded view of the pod assembly of FIG. 13.

FIG. 15 is a partially exploded view of the pod assembly of FIG. 13. Referring to FIG. 15, the first housing section 302 includes a vapor channel 316. The vapor channel 316 is configured to receive the vapor generated during vaping and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the nicotine pre-vapor formulation in the reservoir.

The upstream end of the second housing section 308 defines a pod inlet 322, a first power contact opening 325a, a second power contact opening 325b, a data contact opening 327, a first upstream recess 312a, a second upstream recess 312b, a first pin opening 315a, and a second pin opening 315b. As noted supra, the pod inlet 322 allows air to enter the pod assembly 300 during vaping, while the first power contact opening 325a, the second power contact opening 325b, and the data contact opening 327 are configured to expose the first power contact 324a, the second power contact 324b, and the data contacts 326, respectively, of the connector module 320. In an example embodiment, the first power contact 324a and the second power contact 324b are mounted on a module housing 354 of the connector module 320. In addition, the data contacts 326 may be disposed on a printed circuit board (PCB) 362. Furthermore, the pod inlet 322 may be situated between the first upstream recess 312a and the second upstream recess 312b, while the contact openings (e.g., first power contact opening 325a, second power contact opening 325b, data contact opening 327) may be situated between the first pin opening 315a and the second pin opening 315b. The first pin opening 315a and the second pin opening 315b are configured to accommodate the first activation pin 314a and the second activation pin 314b, respectively, which extend therethrough.

Figure 16:
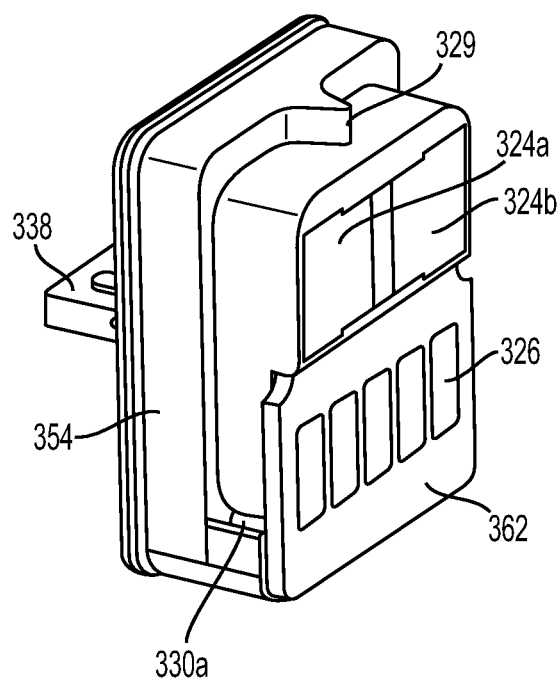
FIG. 16 is a perspective view of the connector module in FIG. 15.
Figure 17:
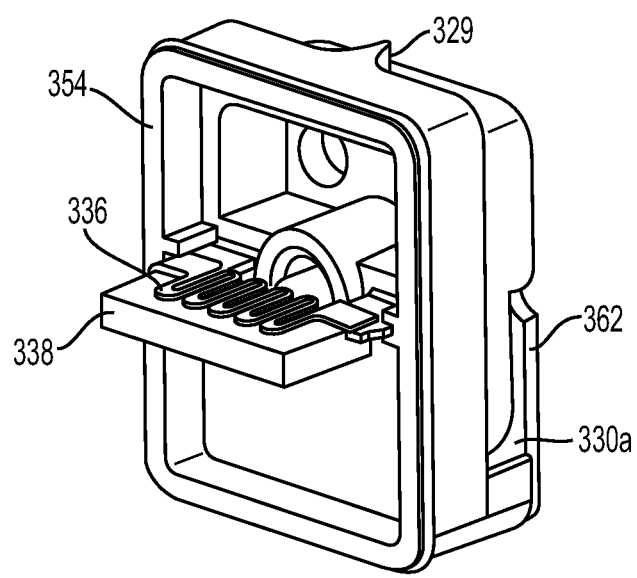
FIG. 17 is another perspective view of the connector module of FIG. 15.

FIG. 16 is a perspective view of the connector module in FIG. 15. FIG. 17 is another perspective view of the connector module of FIG. 16. Referring to FIGS. 16-17, the general framework of the connector module 320 includes a module housing 354. In addition, the connector module 320 has a plurality of faces, including an external face and side faces adjacent to the external face. In an example embodiment, the external face of the connector module 320 is composed of upstream surfaces of the module housing 354, the first power contact 324a, the second power contact 324b, the data contacts 326, and the printed circuit board (PCB) 362. The side faces of the connector module 320 may be integral parts of the module housing 354 and generally orthogonal to the external face.

The pod assembly 300 defines a flow path within from the pod inlet 322 to the pod outlet 304. The flow path through the pod assembly 300 includes, inter alia, a first diverged portion, a second diverged portion, and a converged portion. The pod inlet 322 is upstream from the first diverged portion and the second diverged portion of the flow path. In particular, as shown in FIG. 16, the side face (e.g., inlet side face) of the module housing 354 (and the connector module 320) above the first power contact 324*a* and the second power contact 324*b* is recessed so as to define a divider 329 along with initial segments of the first diverged portion and the second diverged portion of the flow path. In an example embodiment where the divider 329 is indented from the external face of the module housing 354 (e.g., FIG. 16), the side face of the module housing 354 above the first power contact 324*a* and the second power contact 324*b* may also be regarded as defining an inlet portion of the flow path that is downstream from the pod inlet 322 and upstream from the first diverged portion and the second diverged portion of the flow path.

The pair of longer side faces (e.g., vertical side faces) of the module housing 354 is also recessed so as to define subsequent segments of the first diverged portion and the second diverged portion of the flow path. Herein, the pair of longer side faces of the module housing 354 may be referred to, in the alternative, as lateral faces. The sector of the module housing 354 covered by the printed circuit board (PCB) 362 in FIG. 16 (but shown in FIG. 20) defines further segments of the first diverged portion and the second diverged portion along with the converged portion of the flow path. The further segments of the first diverged portion and the second diverged portion include a first curved segment (e.g., first curved path 330*a*) and a second curved segment (e.g., second curved path 330*b*), respectively. As will be discussed in more detail herein, the first diverged portion and the second diverged portion convene to form the converged portion of the flow path.

When the connector module 320 is seated within a receiving cavity in the downstream side of the second housing section 308, the unrecessed side faces of the module housing 354 interface with the sidewalls of the receiving cavity of the second housing section 308, while the recessed side faces of the module housing 354 together with the sidewalls of the receiving cavity define the first diverged portion and the second diverged portion of the flow path. The seating of the connector module 320 within the receiving cavity of the second housing section 308 may be via a close-fit arrangement such that the connector module 320 remains essentially stationary within the pod assembly 300.

As shown in FIG. 17, the connector module 320 includes a wick 338 that is configured to transfer a nicotine pre-vapor formulation to a heater 336. The heater 336 is configured to heat the nicotine pre-vapor formulation during vaping to generate a nicotine vapor. The heater 336 is electrically connected to at least one electrical contact of the connector module 320. For instance, one end (e.g., first end) of the heater 336 may be connected to the first power contact 324*a*, while the other end (e.g., second end) of the heater 336 may be connected to the second power contact 324*b*. In an example embodiment, the heater 336 includes a folded heating element. In such an instance, the wick 338 may have a planar form configured to be held by the folded heating element. When the pod assembly 300 is assembled, the wick 338 is configured to be in fluidic communication with an absorbent material such that the nicotine pre-vapor formulation that will be in the absorbent material (when the pod assembly 300 is activated) will be transferred to the wick 338 via capillary action. In the present specification, a heater may also be referred to as a heating engine.

In an example embodiment, an incoming air flow entering the pod assembly 300 through the pod inlet 322 is directed by the divider 329 into the first diverged portion and the second diverged portion of the flow path. The divider 329 may be wedge-shaped and configured to split the incoming air flow into opposite directions (e.g., at least initially). The split air flow may include a first air flow (that travels through the first diverged portion of the flow path) and a second air flow (that travels through the second diverged portion of the flow path). Following the split by the divider 329, the first air flow travels along the inlet side face and continues around the corner to and along the first lateral face to the first curved path 330*a*. Similarly, the second air flow travels along the inlet side face and continues around the corner to and along the second lateral face to the second curved path 330*b* (e.g., FIG. 20). The converged portion of the flow path is downstream from the first diverged portion and the second diverged portion. The heater 336 and the wick 338 are downstream from the converged portion of the flow path. Thus, the first air flow joins with the second air flow in the converged portion (e.g., converged path 330*c* in FIG. 20) of the flow path to form a combined flow before passing through a module outlet 368 (e.g., labeled in FIG. 18) in the module housing 354 to the heater 336 and the wick 338.

According to at least some example embodiments, the wick 338 may be a fibrous pad or other structure with pores/interstices designed for capillary action. In addition, the wick 338 may have a rectangular shape, although example embodiments are not limited thereto. For instance, the wick 338 may have an alternative shape of an irregular hexagon, wherein two of the sides are angled inward and toward the heater 336. The wick 338 may be fabricated into the desired shape or cut from a larger sheet of material into such a shape. Where the lower section of the wick 338 is tapered towards the winding section of the heater 336 (e.g., hexagon shape), the likelihood of the nicotine pre-vapor formulation being in a part of the wick 338 that continuously evades vaporization (due to its distance from the heater 336) can be reduced or avoided. Furthermore, as noted supra, the heater 336 may include a folded heating element configured to grip the wick 338. The folded heating element may also include at least one prong configured to protrude into the wick 338.

In an example embodiment, the heater 336 is configured to undergo Joule heating (which is also known as ohmic/resistive heating) upon the application of an electric current thereto. Stated in more detail, the heater 336 may be formed of one or more conductors and configured to produce heat when an electric current passes therethrough. The electric current may be supplied from a power source (e.g., battery) within the device body 100 and conveyed to the heater 336 via the first power contact 324*a* or the second power contact 324*b*.

Suitable conductors for the heater 336 include an iron-based alloy (e.g., stainless steel) and/or a nickel-based alloy (e.g., nichrome). The heater 336 may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain the form of the heater 336 shown in the drawings, the winding pattern may be folded so as to grip the wick 338. Additionally, when prongs are part of the heater 336, the projections corresponding to the prongs are bent (e.g., inward and/or orthogonally) before the winding pattern is folded. As a result of the prongs, the possibility that the wick 338 will slip out of the heater 336 will be reduced or prevented. The heater and associated structures are discussed in more detail in U.S.

application Ser. No. 15/729,909, titled "Folded Heater For Electronic Vaping Device", filed Oct. 11, 2017, the entire contents of which is incorporated herein by reference.

Referring to FIG. 15, the first housing section 302 includes a vapor channel 316. The vapor channel 316 is configured to receive nicotine vapor generated by the heater 336 and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the nicotine pre-vapor formulation in the reservoir. Herein, the first housing section 302, the insert 342, and the seal 344 may be referred to collectively as the first section. As will be discussed in more detail herein, the first section is configured to hermetically seal the nicotine pre-vapor formulation until an activation of the pod assembly 300.

According to at least some example embodiments, the insert 342 includes a holder portion that projects from the upstream side and a connector portion that projects from the downstream side. According to at least some example embodiments, the holder portion of the insert 342 is configured to hold an absorbent material, while a connector portion of the insert 342 is configured to engage with the vapor channel 316 of the first housing section 302. The connector portion of the insert 342 may be configured to be seated within the vapor channel 316 and, thus, engage the interior of the vapor channel 316. Alternatively, the connector portion of the insert 342 may be configured to receive the vapor channel 316 and, thus, engage with the exterior of the vapor channel 316. The insert 342 also defines reservoir outlets through which the nicotine pre-vapor formulation flows when the seal 344 is punctured during the activation of the pod assembly 300. The holder portion and the connector portion of the insert 342 may be between the reservoir outlets (e.g., first and second reservoir outlets), although example embodiments are not limited thereto. Furthermore, the insert 342 defines a vapor conduit extending through the holder portion and the connector portion. As a result, when the insert 342 is seated within the first housing section 302, the vapor conduit of the insert 342 will be aligned with and in fluidic communication with the vapor channel 316 so as to form a continuous path through the reservoir to the pod outlet 304 for the nicotine vapor generated by the heater 336 during vaping.

The seal 344 is attached to the upstream side of the insert 342 so as to cover the reservoir outlets in the insert 342. In an example embodiment, the seal 344 defines an opening (e.g., central opening) configured to provide the pertinent clearance to accommodate the holder portion (that projects from the upstream side of the insert 342) when the seal 344 is attached to the insert 342. When the seal 344 is punctured by the first activation pin 314a and the second activation pin 314b of the pod assembly 300, the two punctured sections of the seal 344 will be pushed into the reservoir as flaps, thus creating two punctured openings (e.g., one on each side of the central opening) in the seal 344. The size and shape of the punctured openings in the seal 344 may correspond to the size and shape of the reservoir outlets in the insert 342. In contrast, when in an unpunctured state, the seal 344 may have a planar form and only one opening (e.g., central opening). The seal 344 is designed to be strong enough to remain intact during the normal movement and/or handling of the pod assembly 300 so as to avoid being prematurely/inadvertently breached. For instance, the seal 344 may be a coated foil (e.g., aluminum-backed Tritan).

The second housing section 308 may be structured to contain various components configured to release, receive, and heat the nicotine pre-vapor formulation. For instance, the first activation pin 314a and the second activation pin 314b are configured to puncture the reservoir in the first housing section 302 to release the nicotine pre-vapor formulation. Each of the first activation pin 314a and the second activation pin 314b has a distal end that extends through a corresponding one of the first pin opening 315a and the second pin opening 315b in the second housing section 308. In an example embodiment, the distal ends of the first activation pin 314a and the second activation pin 314b are visible after assembly (e.g., FIG. 13), while the remainder of the first activation pin 314a and the second activation pin 314b are hidden from view within the pod assembly 300. In addition, each of the first activation pin 314a and the second activation pin 314b has a proximal end that is positioned so as to be adjacent to and upstream from the seal 344 prior to activation of the pod assembly 300. When the first activation pin 314a and the second activation pin 314b are pushed into the second housing section 308 to activate the pod assembly 300, the proximal end of each of the first activation pin 314a and the second activation pin 314b will advance through the insert 342 and, as a result, puncture the seal 344, which will release the nicotine pre-vapor formulation from the reservoir. The movement of the first activation pin 314a may be independent of the movement of the second activation pin 314b (and vice versa).

An absorbent material may be downstream from and in fluidic communication with the wick 338. Furthermore, as noted supra, the absorbent material may be configured to engage with a holder portion of the insert 342 (which may project from the upstream side of the insert 342). The absorbent material may have an annular form, although example embodiments are not limited thereto. For example, the absorbent material may resemble a hollow cylinder. In such an instance, the outer diameter of the absorbent material may be substantially equal to (or slightly larger than) the length of the wick 338. The inner diameter of the absorbent material may be smaller than the average outer diameter of the holder portion of the insert 342 so as to result in an interference fit. To facilitate the engagement with the absorbent material, the tip of the holder portion of the insert 342 may be tapered. The absorbent material may be configured to receive and hold a quantity of the nicotine pre-vapor formulation released from the reservoir when the pod assembly 300 is activated. The wick 338 may be positioned within the pod assembly 300 so as to be in fluidic communication with the absorbent material such that the nicotine pre-vapor formulation can be drawn from the absorbent material to the heater 336 via capillary action. The wick 338 may physically contact an upstream side of the absorbent material. In addition, the wick 338 may be aligned with a diameter of the absorbent material, although example embodiments are not limited thereto.

Figure 18:
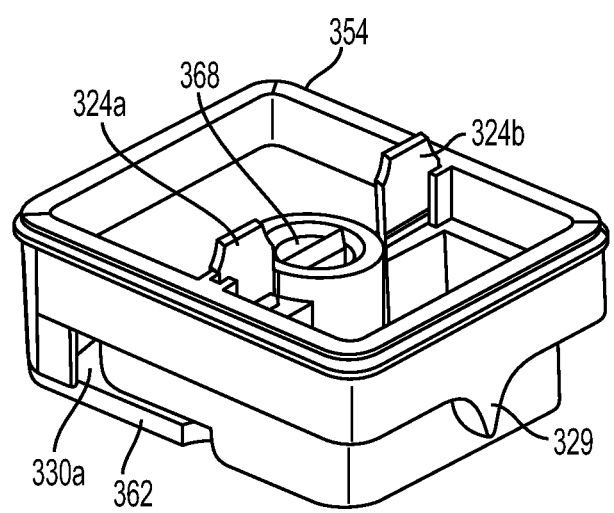
FIG. 18 is a perspective view of the connector module of FIG. 17 without the wick and heater.

As illustrated in FIG. 17, the heater 336 may have a folded configuration so as to grip and establish thermal contact with the opposing surfaces of the wick 338. The heater 336 is configured to heat the wick 338 during vaping to generate a nicotine vapor. To facilitate such heating, the first end of the heater 336 may be electrically connected to the first power contact 324a (FIGS. 16 and 18), while the second end of the heater 336 may be electrically connected to the second power contact 324b (FIGS. 16 and 18). As a result, an electric current may be supplied from a power source (e.g., battery) within the device body 100 and conveyed to the heater 336 via the first power contact 324a or the second power contact 324b. The relevant details of other aspects of the connector module 320 that have already been discussed supra (e.g., in connection with FIGS. 16-17) will not be repeated in this section in the interest of brevity. In an example embodiment, the second housing section 308 includes a receiving cavity for the connector module 320. Collectively, the second housing section 308 and the above-discussed components therein may be referred to as the second section. During vaping, the nicotine vapor generated by the heater 336 is drawn through the vapor conduit of the insert 342, through the vapor channel 316 of the first housing section 302, out the pod outlet 304 of the pod assembly 300, and through the vapor passage 136 of the mouthpiece 102 to the vapor outlet(s).

Figure 19:
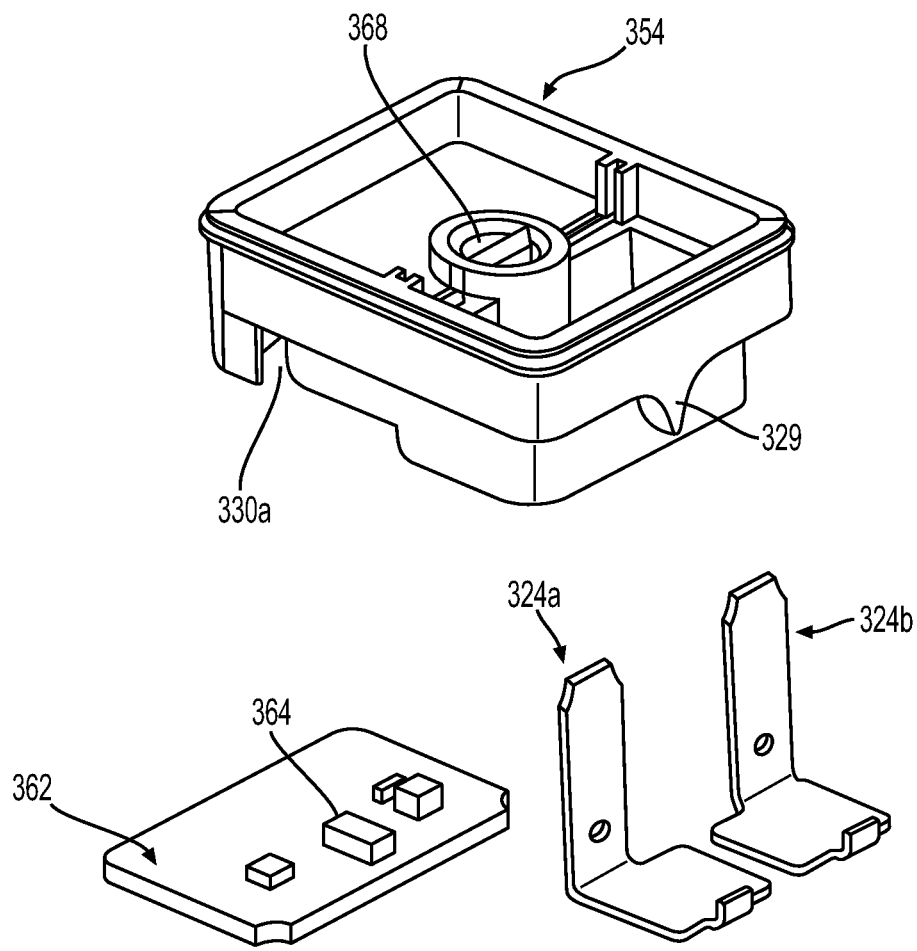
FIG. 19 is an exploded view of the connector module of FIG. 18.
Figure 20:
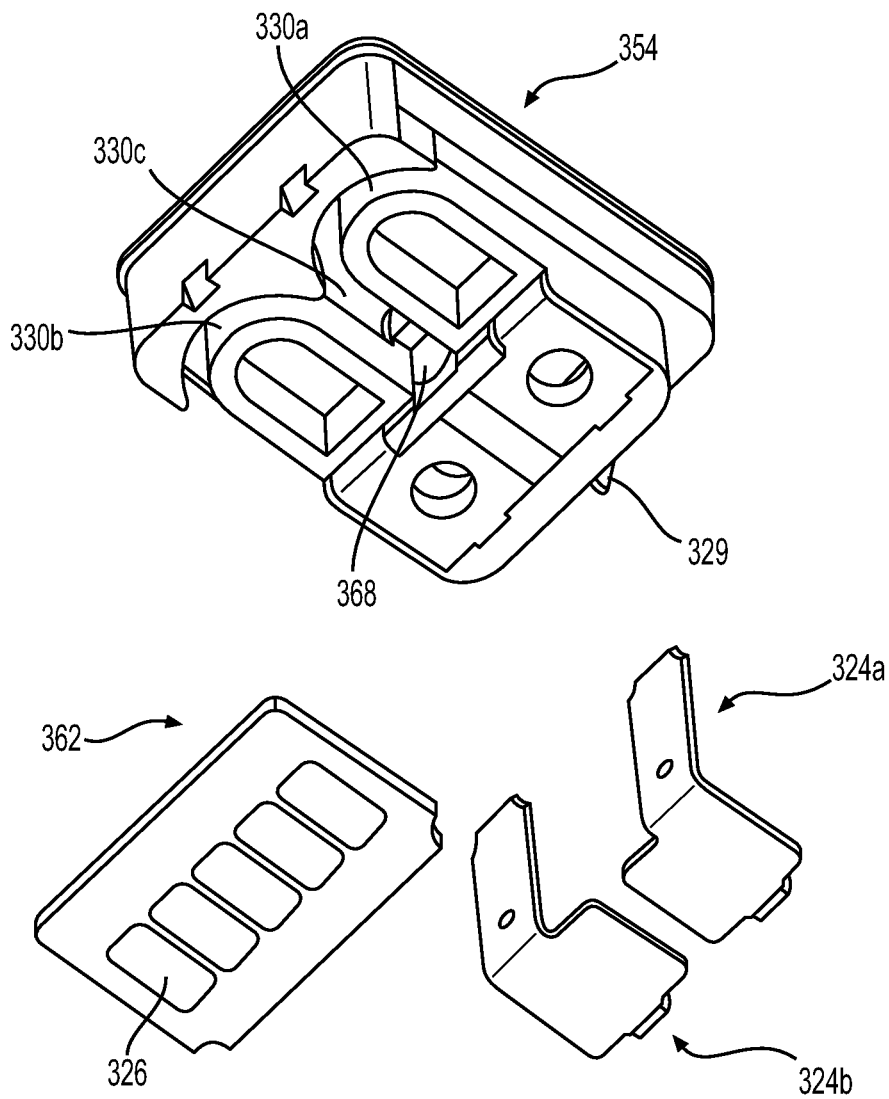
FIG. 20 is another exploded view of the connector module of FIG. 18.

FIG. 18 is a perspective view of the connector module of FIG. 17 without the wick and heater. FIG. 19 is an exploded view of the connector module of FIG. 18. FIG. 20 is another exploded view of the connector module of FIG. 18. Referring to FIGS. 18-20, the module housing 354 forms the framework of the connector module 320. The module housing 354 defines, inter alia, the divider 329 and the flow path for the air drawn into the pod assembly 300. The heating chamber is in fluidic communication with the flow path in the upstream side of the module housing 354 via a module outlet 368.

As noted supra, the flow path for the air drawn into the pod assembly 300 includes a first diverged portion, a second diverged portion, and a converged portion defined by the module housing 354. In an example embodiment, the first diverged portion and the second diverged portion are symmetrical portions bisected by an axis corresponding to the converged portion of the flow path. For instance, as shown in FIG. 20, the first diverged portion, the second diverged portion, and the converged portion may include a first curved path 330a, a second curved path 330b, and a converged path 330c, respectively. The first curved path 330a and the second curved path 330b may be substantially U-shaped paths, while the converged path 330c may be substantially a linear path. Based on an axis corresponding to the converged path 330c and aligned with a crest of the divider 329, the first diverged portion of the flow path may be a mirror image of the second diverged portion of the flow path. During vaping, the air drawn through the pod inlet 322 may be split by the divider 329 and initially flow in opposite directions away from the divider 329, followed by a subsequent flow in parallel before each air stream makes a U-turn (via the first curved path 330a and the second curved path 330b) and convenes (via the converged path 330c) for a combined flow that travels back toward the divider 329 prior to passing through the module outlet 368 to the heating chamber. The heater 336 and the wick 338 may be positioned such that both sides are exposed substantially equally to the combined flow of air passing through the module outlet 368. During vaping, the nicotine vapor generated is entrained by the combined flow of air traveling through the heating chamber to the vapor channel 316.

As illustrated in FIGS. 19-20, each of the first power contact 324a and the second power contact 324b may include a contact face and a contact leg. The contact leg (which may have an elongated configuration) may be oriented orthogonally relative to the contact face (which may be square-shaped), although example embodiments are not limited thereto. The module housing 354 may define a pair of shallow depressions and a pair of apertures to facilitate the mounting of the first power contact 324a and the second power contact 324b. During assembly, the contact face of each of the first power contact 324a and the second power contact 324b may be seated in a corresponding one of the pair of shallow depressions so as to be substantially flush with the external face of the module housing 354 (e.g., FIG. 16). In addition, the contact leg of each of the first power contact 324a and the second power contact 324b may extend through a corresponding one of the pair of apertures so as to protrude from the downstream side of the module housing 354 (e.g., FIG. 18). The heater 336 can be subsequently connected to the contact leg of each of the first power contact 324a and the second power contact 324b.

The printed circuit board (PCB) 362 includes the plurality of data contacts 326 on its upstream side (e.g., FIG. 20) and various electronic components, including a sensor 364, on its downstream side (e.g., FIG. 19). The sensor 364 may be positioned on the printed circuit board (PCB) 362 such that the sensor 364 is within the converged path 330c defined by the module housing 354. In an example embodiment, the printed circuit board (PCB) 362 (and associated components secured thereto) is an independent structure that is initially inserted into the receiving cavity in the downstream side of the second housing section 308 such that the data contacts 326 are exposed by the data contact opening 327 of the second housing section 308. Afterwards, the module housing 354 (with the first power contact 324a, the second power contact 324b, the heater 336, and the wick 338 mounted thereon) may be inserted into the receiving cavity such that the first power contact 324a and the second power contact 324b are exposed by the first power contact opening 325a and the second power contact opening 325b, respectively, of the second housing section 308. Alternatively, to simplify the above two-step insertion process to a one-step insertion process, it should be understood that the printed circuit board (PCB) 362 (and associated components secured thereto) may be affixed to the module housing 354 (e.g., to form a single integrated structure) so as to cover the first curved path 330a, the second curved path 330b, the converged path 330c, and the module outlet 368.

The module outlet 368 may be a resistance-to-draw (RTD) port. In such a configuration, the resistance-to-draw for the nicotine e-vaping device 500 may be adjusted by changing the size of the module outlet 368 (rather than changing the size of the pod inlet 322). In an example embodiment, the size of the module outlet 368 may be selected such that the resistance-to-draw is between 25-100 mmH$_2$O (e.g., between 30-50 mmH$_2$O). For instance, a diameter of 1.0 mm for the module outlet 368 may result in a resistance-to-draw of 88.3 mmH$_2$O. In another instance, a diameter of 1.1 mm for the module outlet 368 may result in a resistance-to-draw of 73.6 mmH$_2$O. In another instance, a diameter of 1.2 mm for the module outlet 368 may result in a resistance-to-draw of 58.7 mmH$_2$O. In yet another instance, a diameter of 1.3 mm for the module outlet 368 may result in a resistance-to-draw of about 40-43 mmH$_2$O. Notably, the size of the module outlet 368, because of its internal arrangement, may be adjusted without affecting the external aesthetics of the pod assembly 300, thereby allowing for a more standardized product design for pod assemblies with various resistance-to-draw (RTD) while also reducing the likelihood of an inadvertent blockage of the incoming air.

Figure 21A:
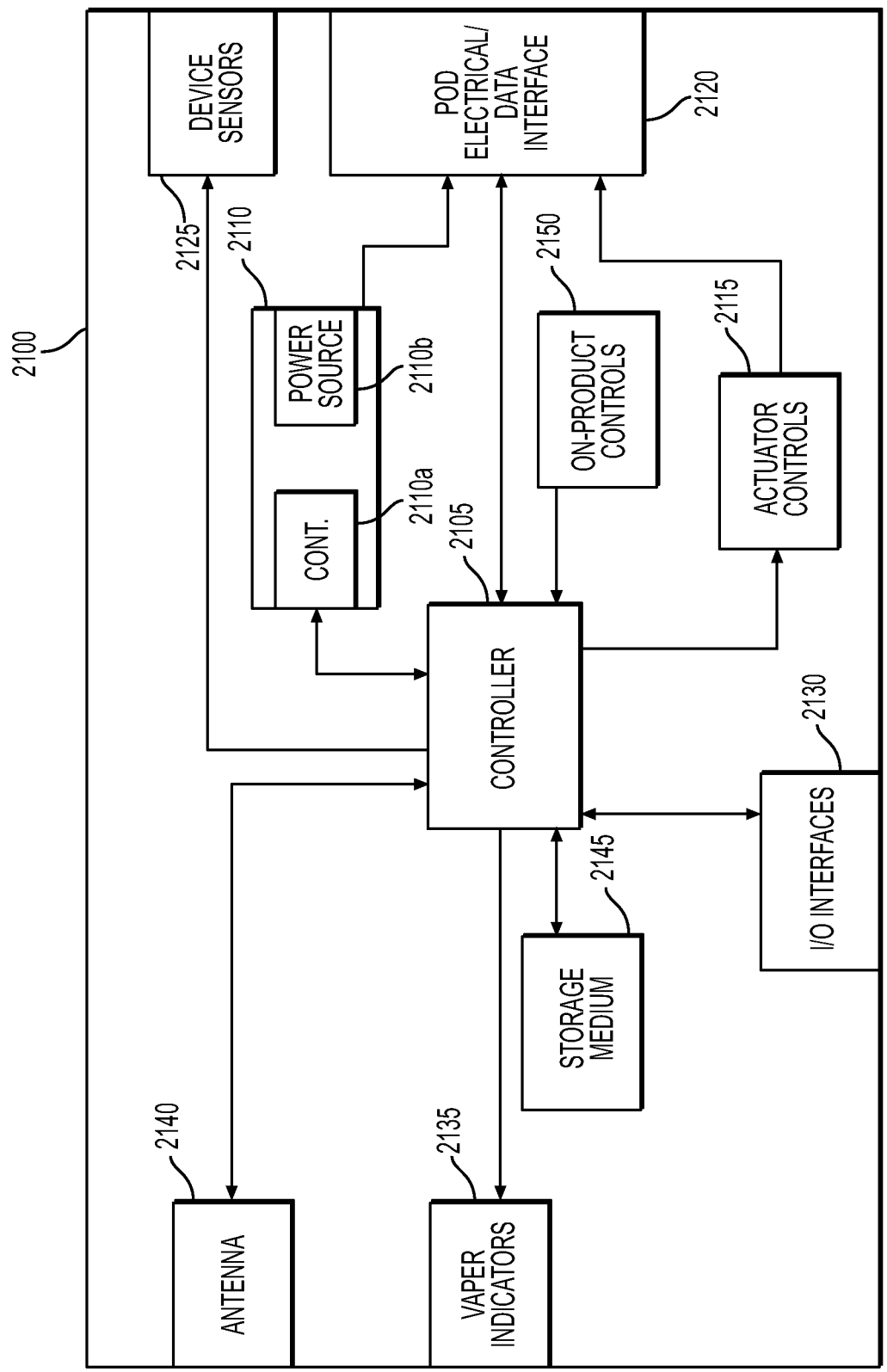
FIG. 21A illustrates a device system diagram of a device body according to an example embodiment.

FIG. 21A illustrates a device system of a device body 100 according to an example embodiment. A device system 2100 may be the system within the device body 100 of the nicotine e-vaping device 500.

The device system 2100 includes a controller 2105, a power supply 2110, actuator controls 2115, a pod electrical/data interface 2120, device sensors 2125, input/output (I/O) interfaces 2130, vaper indicators 2135, at least one antenna 2140 and a storage medium 2145. The device system 2100 is not limited to the features shown in FIG. 21A. For example, the device system 2100 may include additional elements. However, for the sake of brevity, the additional elements are not described. In other example embodiments, the device system 2100 may not include an antenna.

The controller 2105 may be hardware, firmware, hardware executing software or any combination thereof. When the controller 2105 is hardware, such existing hardware may include one or more Central Processing Units (CPUs), microprocessors, processor cores, multiprocessors, digital signal processors (DSPs), application-specific-integrated-circuits (ASICs), field programmable gate arrays (FPGAs) computers or the like configured as special purpose machines to perform the functions of the controller 2105. CPUs, microprocessors, processor cores, multiprocessors, DSPs, ASICs and FPGAs may generally be referred to as processing devices.

In the event where the controller 2105 is, or includes, a processor executing software, the controller 2105 is configured as a special purpose machine (e.g., a processing device) to execute the software, stored in memory accessible by the controller 2105 (e.g., the storage medium 2145 or another storage device), to perform the functions of the controller 2105. The software may be embodied as program code including instructions for performing and/or controlling any or all operations described herein as being performed by the controller 2105 or the controller 2105A (FIG. 21B).

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Figure 21B:
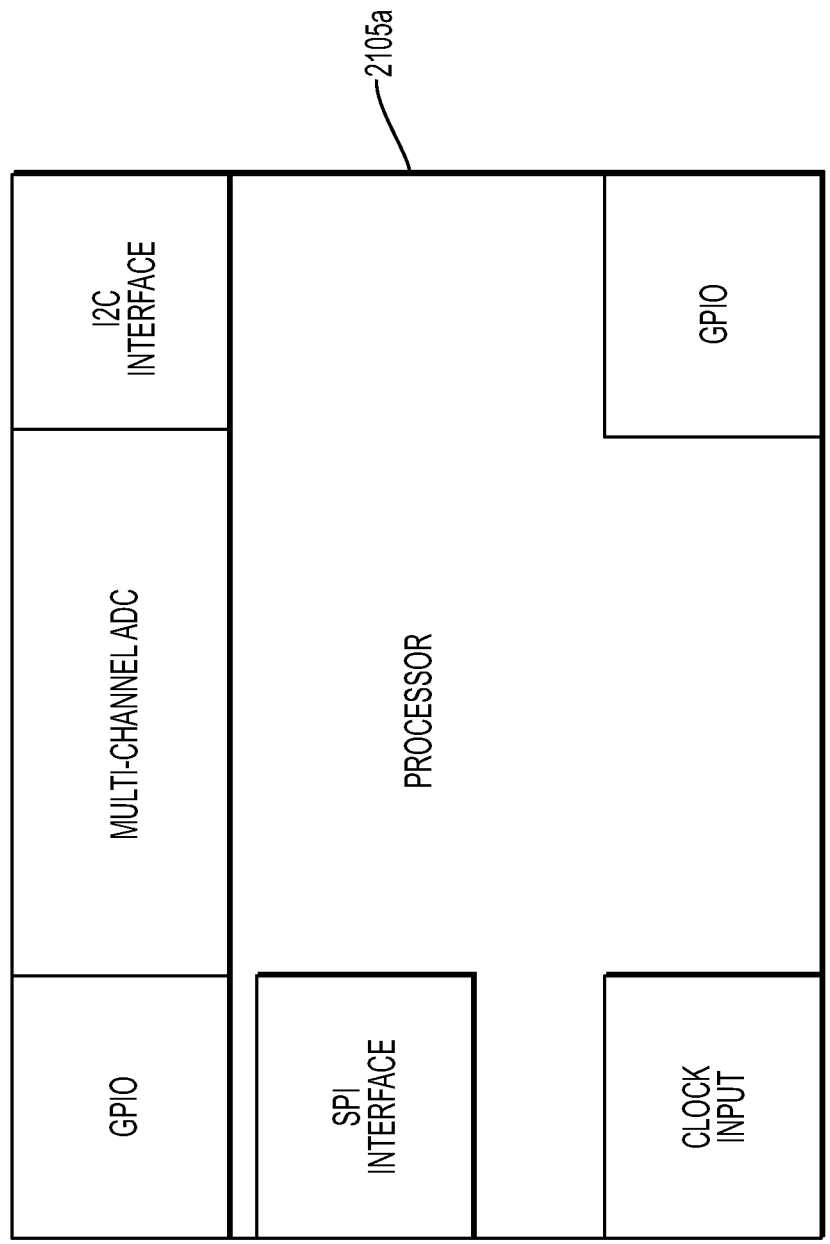
FIG. 21B illustrates an example of a microprocessor according to an example embodiment.

FIG. 21B illustrates an example of a controller 2105A according to an example embodiment. According to an example embodiment, the controller 2105A illustrated in FIG. 21B is an example implementation of the controller 2105 illustrated in FIG. 21A. The controller 2105A may be on include a microprocessor. Further, the controller 2105A may include input/output interfaces, such as general purpose input/outputs (GPIOs), inter-integrated circuit (I$^2$C) interfaces, serial peripheral interface bus (SPI) interfaces, or the like; a multichannel analog-to-digital converter (ADC); and a clock input terminal, as is shown in FIG. 21B. However, example embodiments should not be limited to this example. For example, the controller 2105A may further include a digital-to-analog converter and arithmetic circuitry or circuits.

Returning to FIG. 21A, the controller 2105 communicates with the power supply 2110, the actuator control 2115, the pod electrical/data interface 2120, the device sensors 2125, the input/output (I/O) interfaces 2130, the vaper indicators 2135, on-product controls 2150, and the at least one antenna 2140. According to at least some example embodiments, the on-product controls 2150 can include any device or devices capable of being manipulated manually by an adult vaper to indicate a selection of a value. Example implementations include, but are not limited to, one or more buttons, a dial, a capacitive sensor, and a slider.

The controller 2105 communicates with a cryptographic coprocessor with non-volatile memory (CC-NVM) or non-volatile memory (NVM) in the pod assembly 300 through the pod electrical/data interface 2120. The term CC-NVM may refer to a hardware module (s) including a processor for encryption and related processing and an NVM. More specifically, the controller 2105 may utilize encryption to authenticate the pod assembly 300. As will be described, the controller 2105 communicates with the CC-NVM package or NVM to authenticate the pod assembly 300. More specifically, the non-volatile memory may be encoded during manufacture with product and other information for authentication.

The memory device may be coded with an electronic identity to permit at least one of an authentication of the pod assembly 300 and a pairing of operating parameters specific to a type of the pod assembly 300 (or physical construction, such as a heating engine type) when the pod assembly 300 is inserted into the device body 100. In addition to authenticating based on an electronic identity of the pod assembly 300, the controller 2105 may authorize use of the pod assembly 300 based on an expiration date of the stored nicotine pre-vapor formulation and/or heater encoded into the NVM or the non-volatile memory of the CC-NVM. If the controller determines that the expiration date encoded into the non-volatile memory has passed, the controller may not authorize use of the pod assembly 300 and disable the nicotine e-vaping device 500.

The controller 2105 (or storage medium 2145) stores key material and proprietary algorithm software for the encryption. For example, encryption algorithms rely on the use of random numbers. The security of these algorithms depends on how truly random these numbers are. These numbers are usually pre-generated and coded into the processor or memory devices. Example embodiments may increase the randomness of the numbers used for the encryption by using the vapor drawing parameters e.g., durations of instances of vapor drawing, intervals between instances of vapor drawing, or combinations of them, to generate numbers that are more random and more varying from individual to individual than pre-generated random numbers. All communications between the controller 2105 and the pod assembly 300 may be encrypted.

Moreover, the pod assembly 300 can be used as a general pay-load carrier for other information such as software patches for the nicotine e-vaping device 500. Since encryption is used in all the communications between the pod assembly 300 and the controller 2105, such information is more secure and the nicotine e-vaping device 500 is less prone to being installed with malwares or viruses. Use of the CC-NVM as an information carrier such as data and software updates allows the nicotine e-vaping device 500 to be updated with software without it being connected to the Internet and for an adult vaper to go through a downloading process as with most other consumer electronics devices requiring periodic software updates.

The controller 2105 may also include a cryptographic accelerator to allow resources of the controller 2105 to perform functions other than the encoding and decoding involved with the authentication. The controller 2105 may also include other security features such as preventing unauthorized use of communication channels and preventing unauthorized access to data if a pod or adult vaper is not authenticated.

In addition to a cryptographic accelerator, the controller 2105 may include other hardware accelerators. For example, the controller 2105 may include a floating point unit (FPU), a separate DSP core, digital filters and Fast Fourier Transform (FFT) modules.

The controller 2105 is configured to operate a real time operating system (RTOS), control the device system 2100 and may be updated through communicating with the NVM or CC-NVM or when the device system 2100 is connected with other devices (e.g., a smart phone) through the I/O interfaces 2130 and/or the antenna 2140. The I/O interfaces 2130 and the antenna 2140 allow the device system 2100 to connect to various external devices such as smart phones, tablets, and PCs. For example, the I/O interfaces 2130 may include a micro-USB connector. The micro-USB connector may be used by the device system 2100 to charge the power source 2110b.

The controller 2105 may include on-board RAM and flash memory to store and execute code including analytics, diagnostics and software upgrades. As an alternative, the storage medium 2145 may store the code. Additionally, in another example embodiment, the storage medium 2145 may be on-board the controller 2105.

The controller 2105 may further include on-board clock, reset and power management modules to reduce an area covered by a PCB in the device body 100.

The device sensors 2125 may include a number of sensor transducers that provide measurement information to the controller 2105. The device sensors 2125 may include a power supply temperature sensor, an external pod temperature sensor, a current sensor for the heater, power supply current sensor, air flow sensor and an accelerometer to monitor movement and orientation. The power supply temperature sensor and external pod temperature sensor may be a thermistor or thermocouple and the current sensor for the heater and power supply current sensor may be a resistive based sensor or another type of sensor configured to measure current. The air flow sensor may be a microelectromechanical system (MEMS) flow sensor or another type of sensor configured to measure air flow such as a hot-wire anemometer. Further, as will be discussed in greater detail below with reference to FIGS. 22A-26, instead of, or in addition to, measuring air flow using a flow sensor included in the device sensors 2125 of the device system 2100 of the device body 100, air flow may be measured using a hot wire anemometer 2220A located in pod system 2200 of the pod assembly 300.

The data generated from one or more of the device sensors 2125 may be sampled at a sample rate appropriate to the parameter being measured using a discrete, multi-channel analog-to-digital converter (ADC).

The controller 2105 may adapt heater profiles for a nicotine pre-vapor formulation and other profiles based on the measurement information received from the controller 2105. For the sake of convenience, these are generally referred to as vaping or vapor profiles. The heater profile identifies the power profile to be supplied to the heater during the few seconds when vapor drawing takes place. For example, a heater profile can deliver maximum power to the heater when an instance of vapor drawing is initiated, but then after a second or so immediately reduce the power to half way or a quarter way. According to at least some example embodiments, the modulation of electrical power provided to the heater is may be implemented using pulse width modulation.

In addition, a heater profile can also be modified based on a negative pressure applied on the nicotine e-vaping device 500. The use of the MEMS flow sensor allows vapor drawing strength to be measured and used as feedback to the controller 2105 to adjust the power delivered to the heater of the pod, which may be referred to as heating or energy delivery.

According to at least some example embodiments, when the controller 2105 recognizes the pod is currently installed (e.g., via SKU), the controller 2105 matches an associated heating profile that is designed for that particular pod. The controller 2105 and the storage medium 2145 will store data and algorithms that allow the generation of heating profiles for all SKUs. In another example embodiment, the controller 2105 may read the heating profile from the pod. The adult vapers may also adjust heating profiles to suit their preferences.

As shown in FIG. 21A, the controller 2105 sends data to and receives data from the power supply 2110. The power supply 2110 includes a power source 2110b and a power controller 2110a to manage the power output by the power source 2110b.

The power source 2110b may be a Lithium-ion battery or one of its variants, for example a Lithium-ion polymer battery. Alternatively, the power source 2110b may be a Nickel-metal hydride battery, a Nickel cadmium battery, a Lithium-manganese battery, a Lithium-cobalt battery or a fuel cell. Alternatively, the power source 2110b may be rechargeable and include circuitry allowing the battery to be chargeable by an external charging device. In that case, the circuitry, when charged, provides power for a desired (or alternatively a pre-determined) number of instances of vapor drawing, after which the circuitry must be re-connected to an external charging device.

The power controller 2110a provides commands to the power source 2110b based on instructions from the controller 2105. For example, the power supply 2110 may receive a command from the controller 2105 to provide power to the pod (through the pod electrical/data interface 2120) when the pod is authenticated and the adult vaper activates the device system 2100 (e.g., by activating a switch such as a toggle button, capacitive sensor, IR sensor). When the pod is not authenticated, the controller 2105 may either send no command to the power supply 2110 or send an instruction to the power supply 2110 to not provide power. In another example embodiment, the controller 2105 may disable all operations of the device system 2100 if the pod is not authenticated.

In addition to supplying power to the pod, the power supply 2110 also supplies power to the controller 2105. Moreover, the power controller 2110a may provide feedback to the controller 2105 indicating performance of the power source 2110b.

The controller 2105 sends data to and receives data from the at least one antenna 2140. The at least one antenna 2140 may include a Near Field Communication (NFC) modem and a Bluetooth Low Energy (LE) modem and/or other modems for other wireless technologies (e.g., Wi-Fi). In an example embodiment, the communications stacks are in the modems, but the modems are controlled by the controller 2105. The Bluetooth LE modem is used for data and control communications with an application on an external device (e.g., smart phone). The NFC modem may be used for pairing of the nicotine e-vaping device 500 to the application and retrieval of diagnostic information. Moreover, the Bluetooth LE modem may be used to provide location information (for an adult vaper to find the nicotine e-vaping device 500) or authentication during a purchase.

As described above, the device system 2100 may generate and adjust various profiles for vaping. The controller 2105 uses the power supply 2110 and the actuator controls 2115 to regulate the profile for the adult vaper.

The actuator controls 2115 include passive and active actuators to regulate a desired vapor profile. For example, the device body 100 may include an inlet channel within a mouthpiece. The actuator controls 2115 may control the inlet channel based on commands from the controller 2105 associated with the desired vapor profile.

Moreover, the actuator controls 2115 are used to energize the heater in conjunction with the power supply 2110. More specifically, the actuator controls 2115 are configured to generate a drive waveform associated with the desired vaping profile. As described above, each possible profile is associated with a drive waveform. Upon receiving a command from the controller 2105 indicating the desired vaping profile, the actuator controls 2115 may produce the associated modulating waveform for the power supply 2110.

The controller 2105 supplies information to the vaper indicators 2135 to indicate statuses and occurring operations to the adult vaper. The vaper indicators 2135 include a power indicator (e.g., LED) that may be activated when the controller 2105 senses a button pressed by the adult vaper. The vaper indicators 2135 may also include a vibrator, speaker, an indicator for a current state of an adult vaper-controlled vaping parameter (e.g., nicotine vapor volume) and other feedback mechanisms.

Once the pod assembly 300 is authenticated, the controller 2105 operates the power supply 2110, the actuator controls 2115, vaper indicators 2135 and antenna 2140 in accordance with the adult vaper using the nicotine e-vaping device 500 and the information stored by the NVM or CC-NVM on the pod. Moreover, the controller 2105 may include logging functions and be able to implement algorithms to calibrate the nicotine e-vaping device 500. The logging functions are executed by the controller 2105 to record usage data as well any unexpected events or faults. The recorded usage data may be used for diagnostics and analytics. The controller 2105 may calibrate the nicotine e-vaping device 500 using buttonless vaping (i.e., vaping without pressing a button such as generating a nicotine vapor when a negative pressure is applied on the mouthpiece), an adult vaper configuration and the stored information on the CC-NVM or NVM including vapor drawing sensing, nicotine pre-vapor formulation level and nicotine pre-vapor formulation composition. For example, the controller 2105 may command the power supply 2110 to supply power to the heater in the pod based on a vaping profile associated with the nicotine pre-vapor formulation composition in the pod. Alternatively, a vaping profile may be encoded in the CC-NVM or NVM and utilized by the controller 2105.

Figure 22A:
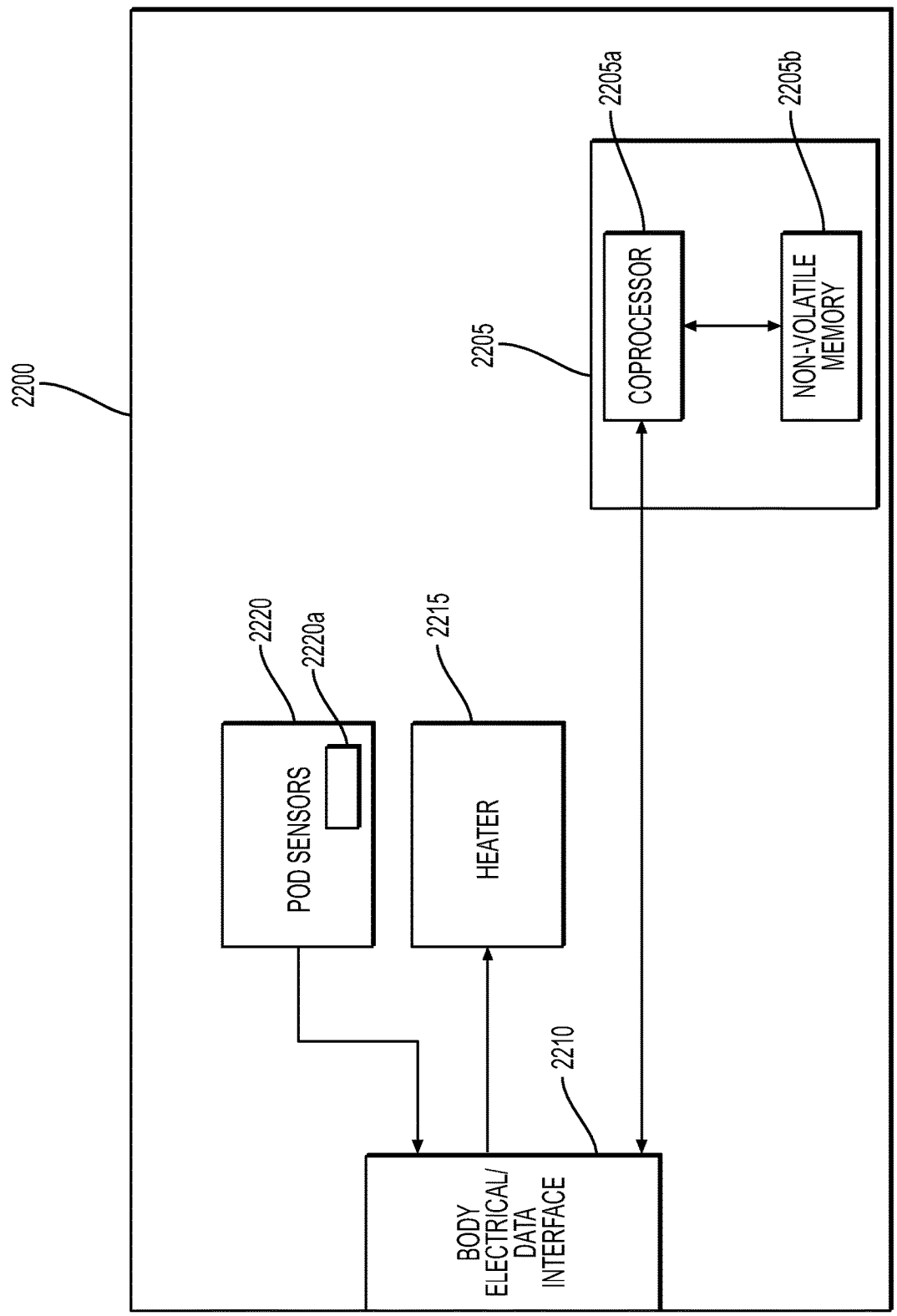
FIG. 22A illustrates a pod system diagram of a pod assembly according to an example embodiment.

FIG. 22A illustrates a pod system diagram according to an example embodiment. A pod system 2200 may be the system within the pod assembly 300.

As shown in FIG. 22A, the pod system 2200 includes a CC-NVM 2205, a body electrical/data interface 2210, a heater 2215 and pod sensors 2220. The pod system 2200 communicates with the device system 2100 through the body electrical/data interface 2210 and the pod electrical/data interface 2120. The CC-NVM 2205 includes a cryptographic coprocessor 2205a and a non-volatile memory 2205b. The controller 2105 may access the information stored on the non-volatile memory 2205b for the purposes of authentication and operating the pod assembly 300 by communicating with the cryptographic coprocessor 2205a.

In another example embodiment, the pod assembly 300 may not have a cryptographic coprocessor. For example, FIG. 22B illustrates an example of the pod system of FIG. 22A in which the cryptographic coprocessor 2205a is omitted, according to an example embodiment, and FIG. 23 illustrates an example of the pod system 22B connected to the device system of FIG. 21A according to an example embodiment.

Figure 22B:
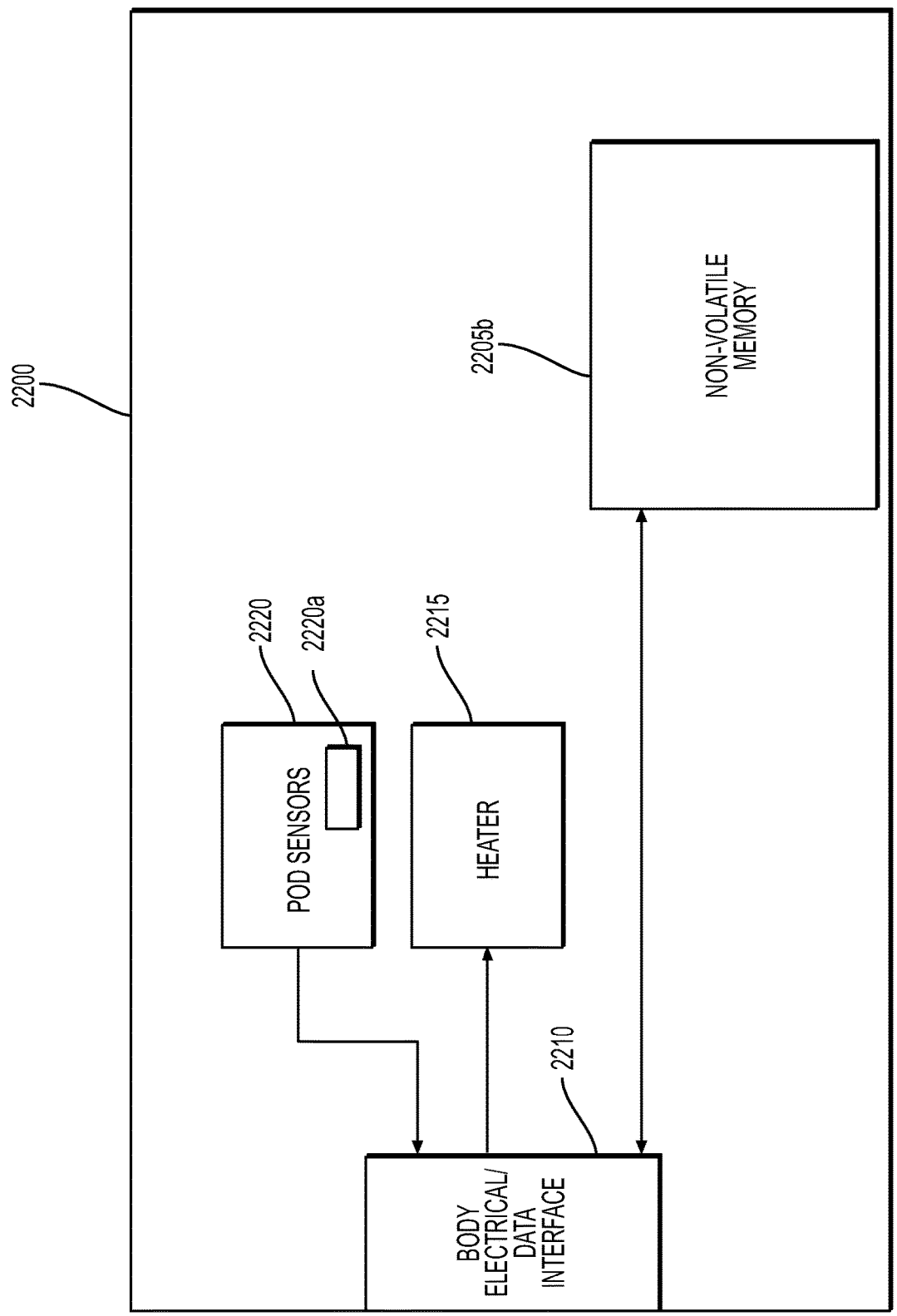
FIG. 22B illustrates an example of the pod system of FIG. 22A in which a cryptographic coprocessor is omitted, according to an example embodiment.
Figure 23:
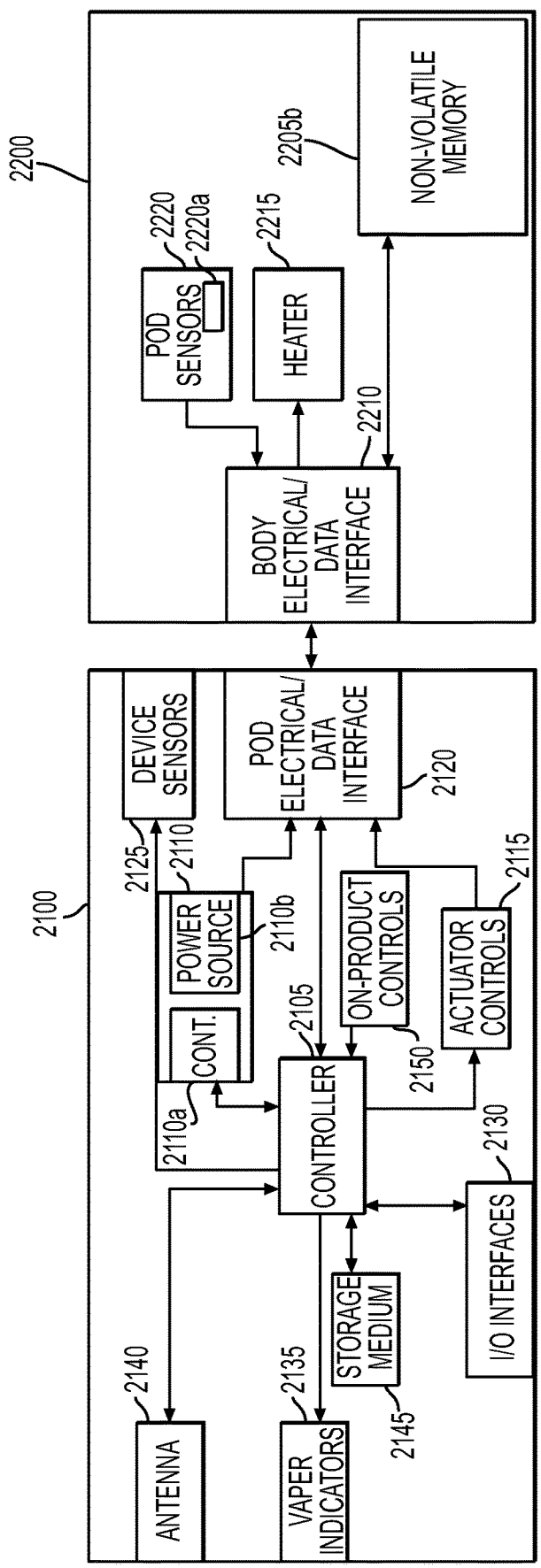
FIG. 23 illustrates a pod system connected to a device system according to an example embodiment.

As is shown in FIG. 22B, the pod system 2200 may include the non-volatile memory 2205b in place of the CC-NVM 2205, and the cryptographic coprocessor 2205a is omitted. When no cryptographic coprocessor exists in the pod system 2200, the controller 2105 may read data from the non-volatile memory 2205b without use of the cryptographic coprocessor to control/define the heating profile.

The non-volatile memory 2205b may be coded with an electronic identity to permit at least one of an authentication of the pod and a pairing of operating parameters specific to a type of the pod when the pod assembly is inserted into the through-hole of the device body 100. In addition to authenticating based on an electronic identity of the pod, the controller 2105 may authorize use of the pod based on an expiration date of the stored nicotine pre-vapor formulation and/or encoded into the non-volatile memory 2205b. If the controller determines that the expiration date encoded into the non-volatile memory non-volatile memory 2205b has passed, the controller may not authorize use of the pod and disable the nicotine e-vaping device 500.

Moreover, the non-volatile memory 2205b may store information such as a stock keeping unit (SKU) of the nicotine pre-vapor formulation in the nicotine pre-vapor formulation compartment (including nicotine pre-vapor formulation composition), software patches for the device system 2100, product usage information such as vapor drawing instance count, vapor drawing instance duration, and nicotine pre-vapor formulation level. The non-volatile memory 2205b may store operating parameters specific to the type of the pod and the nicotine pre-vapor formulation composition. For example, the non-volatile memory 2205b may store the electrical and mechanical design of the pod for use by the controller 2105 to determine commands corresponding to a desired vaping profile.

The nicotine pre-vapor formulation level in the pod may be determined in one of two ways, for example. In one example embodiment, one of the pod sensors 2220 directly measures the nicotine pre-vapor formulation level in the pod.

In another example embodiment, the non-volatile memory 2205b stores the vapor drawing instance count from the pod and the controller 2105 uses the vapor drawing instance count as a proxy to the amount of nicotine pre-vapor formulation vaporized.

The controller 2105 and/or the storage medium 2145 may store nicotine pre-vapor formulation calibration data that identifies an operating point for the nicotine pre-vapor formulation composition. The nicotine pre-vapor formulation calibration data include data describing how nicotine pre-vapor formulation flow rate changes with a remaining nicotine pre-vapor formulation level or how volatility changes with an age of the nicotine pre-vapor formulation and may be used for calibration by the controller 2105. The nicotine pre-vapor formulation calibration data may be stored by the controller 2105 and/or the storage medium 2145 in a table format. The nicotine pre-vapor formulation calibration data allows the controller 2105 to equate the vapor drawing instance count to the amount of nicotine pre-vapor formulation vaporized.

The controller 2105 writes the nicotine pre-vapor formulation level and vapor drawing instance count back to the non-volatile memory 2205*b* in the pod so if the pod is removed from the device body 100 and later on re-installed, an accurate nicotine pre-vapor formulation level of the pod will still be known by the controller 2105.

The operating parameters (e.g., power supply, power duration, air channel control) are referred to as a vaping profile. Moreover, the non-volatile memory 2205*b* may record information communicated by the controller 2105. The non-volatile memory 2205*b* may retain the recorded information even when the device body 100 becomes disconnected from the pod.

In an example embodiment, the non-volatile memory 2205*b* may be a programmable read only memory.

The heater 2215 is actuated by the controller 2105 and transfers heat to at least a portion of the nicotine pre-vapor formulation in the pod assembly 300, for example, in accordance with the commanded profile (volume, temperature (based on power profile) and flavor) from the controller 2105.

The heater 2215 may be a planar body, a ceramic body, a single wire, a cage of resistive wire, a wire coil surrounding a wick, a mesh, a surface or any other suitable form for example. Examples of suitable electrically resistive materials include titanium, zirconium, tantalum and metals from the platinum group. Examples of suitable metal alloys include stainless steel, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 2215 comprises at least one material selected from the group consisting of stainless steel, copper, copper alloys, nickel-chromium alloys, superalloys and combinations thereof. In an embodiment, the heater 2215 is formed of nickel-chromium alloys or iron-chromium alloys. In one embodiment, the heater 2215 can be a ceramic heater having an electrically resistive layer on an outside surface thereof.

In another embodiment, the heater 2215 may be constructed of an iron-aluminide (e.g., FeAl or $Fe_3Al$), such as those described in commonly owned U.S. Pat. No. 5,595,706 to Sikka et al. filed Dec. 29, 1994, or nickel aluminides (e.g., $Ni_3Al$), the entire contents of which are hereby incorporate by reference.

The heater 2215 may determine an amount of nicotine pre-vapor formulation to heat based on feedback from the pod sensors or the controller 2105. The flow of nicotine pre-vapor formulation may be regulated by a micro-capillary or wicking action. Moreover, the controller 2105 may send commands to the heater 2215 to adjust an air inlet to the heater 2215.

The data generated from the pod sensors 2220 may be sampled at a sample rate appropriate to the parameter being measured using a discrete, multi-channel analog-to-digital converter (ADC). The pod sensors 2220 may include, for example, a heater temperature sensor, nicotine pre-vapor formulation flow rate monitor, an air flow sensor and a puff detector. According to at least one example embodiment, the heater temperature sensor may be a thermistor or thermocouple and the nicotine pre-vapor formulation flow rate sensing may be performed by the pod system 2200 using electrostatic interference or an in-nicotine pre-vapor formulation rotator.

Pod sensors 2220 may also include a hot wire anemometer (HWA) 2220A. The HWA 2220A provides an air flow rate sensing function and may also be referred to in the present specification as the flow sensor 2220A. Further, as is discussed in greater detail below in FIGS. 24A-27, according to at least some example embodiments, the hot wire anemometer (HWA) 2220A may use a single heated element in conjunction with a dual control loop architecture to facilitate any or all of (i) air flow rate sensing, (ii) puff detection, and (iii) ambient temperature tracking. For example, in at last some conventional systems that include an HWA, the HWAs are intended to measure continuous flow, and thus, two or more sensing elements are used: one to measure the ambient temperature and the other to measure the rate of heat transfer from some heated element. Consequently, by performing air flow rate sensing and ambient temperature tracking using a single heated element, a complexity of hardware (e.g., circuitry) needed to perform both air flow rate sensing and ambient temperature tracking may be advantageously reduced. Further, the ability to track the ambient temperature of the HWA 2220A is also useful because the effect of the nearby heating engine can be taken into account when estimating the temperature of the heated element of the HWA 2220A.

As used in the present specification, the term "ambient temperature" when used with respect to an HWA or a flow sensor may refer to a temperature of air in an immediate vicinity of the HWA or flow sensor. For example, when at least the heated element of the HWA (or flow sensor) 2220A is inside in the pod assembly 300, the ambient temperature of the HWA (or flow sensor) 2220A may refer to a temperature of the air within the pod assembly 300 surrounding the heated element of the HWA (or flow sensor 2220A). According to at least some example embodiments, if a temperature of the air within the pod assembly 300 is substantially uniform (e.g., when nicotine vapor is not currently being drawn through outlets of the nicotine e-vaping device 500 and/or when the heater 2215 is not currently being actuated), a reference to the "ambient temperature" of the HWA (or flow sensor) 2220A in the present specification may refer to a temperature of the air within the pod assembly 300, generally.

As will be discussed in greater detail below with reference to FIGS. 24A-26, the HWA 2220A includes a heated element which becomes heated as a result of applying power to the heated element. Further, the temperature of the heated element affects the resistance (SI) of the heated element. Consequently, a voltage of the heated element may be used to estimate a temperature of the heated element. Further, in the presence of flowing air, heat will be carried away from the heated element of the HWA 2220A by the flowing air, and thus, a level of power needed to cause the heated element of the HWA 2220A to maintain a particular temperature can be used to estimate an air flow rate of air flowing around the heated element of the HWA 2220A. As used in the present specification, air flowing through the space in an immediate vicinity of the heated element of the HWA (or flow sensor) 2220A may be referred to, simply, as air flowing around the HWA (or flow sensor) 2220A or air flowing around the heated element of the HWA (or flow sensor) 2220A. Examples of the heated element of the HWA 2220A will now be discussed in greater detail below with reference to FIGS. 24A-24D.

According to at least some example embodiments, the HWA 2220A may be (or be included in) the sensor 364 of FIG. 19. Consequently, as is noted above with reference to the sensor 364, and FIGS. 19 and 20, the HWA 2220A may be situated within the converged path 330c. Further, as is described above with reference to FIGS. 19 and 20, the converged path 330c is a portion of a flow path of air that is drawn into the pod assembly 300 through pod inlet 322 and exits the module outlet 368 atop which the heater 336 sits (FIG. 17). Thus, according to at least some example embodiments, the air that flows around the HWA 2220A is air that flows from the pod inlet 322 to the module outlet 368 via the converged path 330c (e.g., during a puff).

Figure 24A:
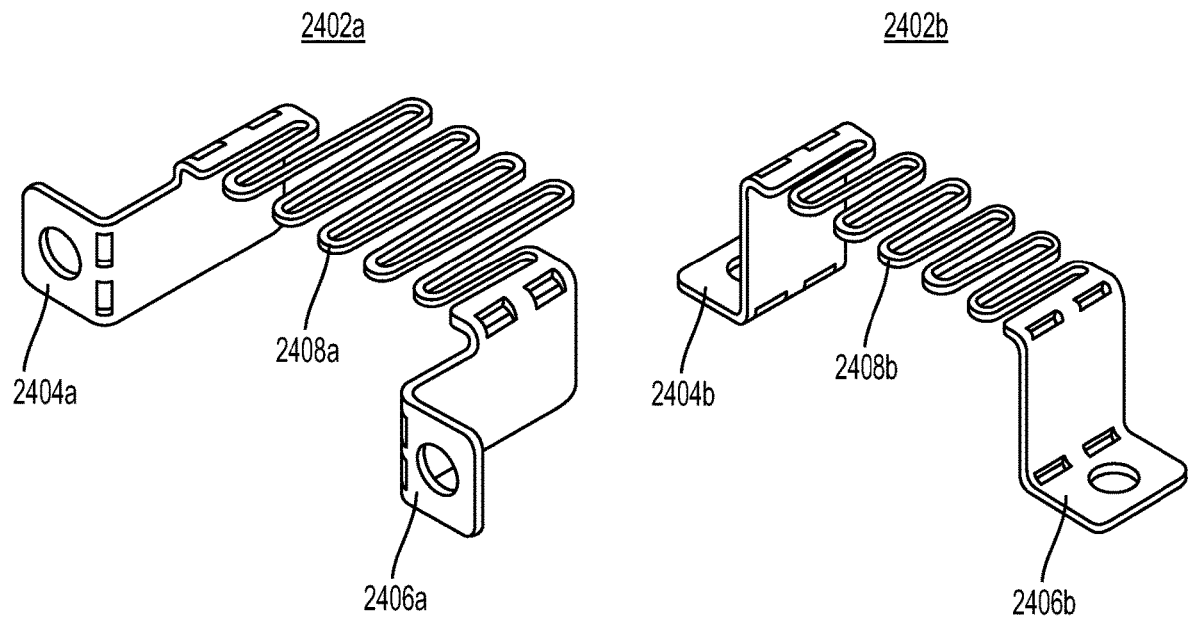
FIGS. 24A-24D illustrate example implementations of a heated element included in a hot wire anemometer (HWA) of the pod systems of FIG. 22A according to an example embodiment.
Figure 24B:
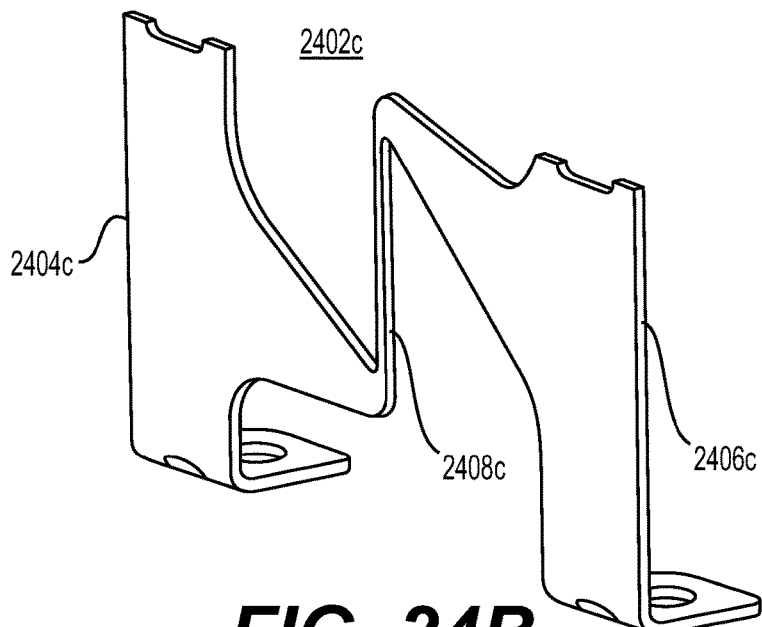
Figure 24C:
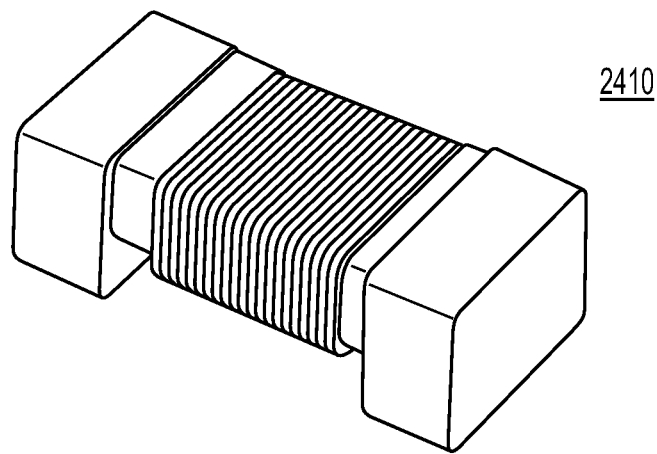
Figure 24D:
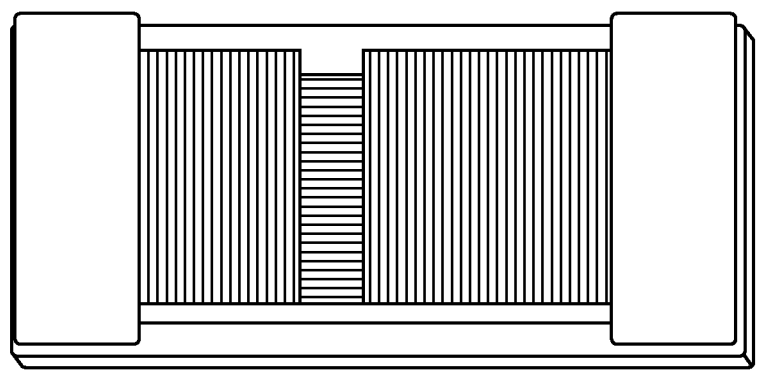

FIGS. 24A-24D illustrate example implementations of the heated element included in the HWA 2220A. Referring to FIG. 24A, the heated element of the HWA 2220A may be implemented by a first etched serpentine element 2402A or a second etched serpentine element 2402B. As is illustrated in FIG. 24A, the first etched serpentine element 2402A includes a first serpentine wire 2408A suspended between a first support 2404A and a second support 2406A, and the second etched serpentine element 2402B includes a second serpentine wire 2408B suspended between a third support 2404B and a fourth support 2406B. Referring to FIG. 24B, the heated element of the HWA 2220A may be implemented by a single-wire element 2402C. As is illustrated in FIG. 24B, the single-wire element includes a single wire 2408C vertically suspended between a fifth support 2404C and a sixth support 2406C. Referring to FIG. 24C, the heated element of the HWA 2220A may be implemented by a wire-wound element 2410. For example, the wire-wound element 2410 may be a Coilcraft wire-wound surface mount (SMT) inductor. Referring to FIG. 24D, the heated element of the HWA 2220A may be implemented by a thin film resistance temperature detector (RTD) 2412. A dual control loop architecture according to at least some example embodiments will now be discussed below with reference to FIGS. 25A-25D and 26.

Figure 25A:
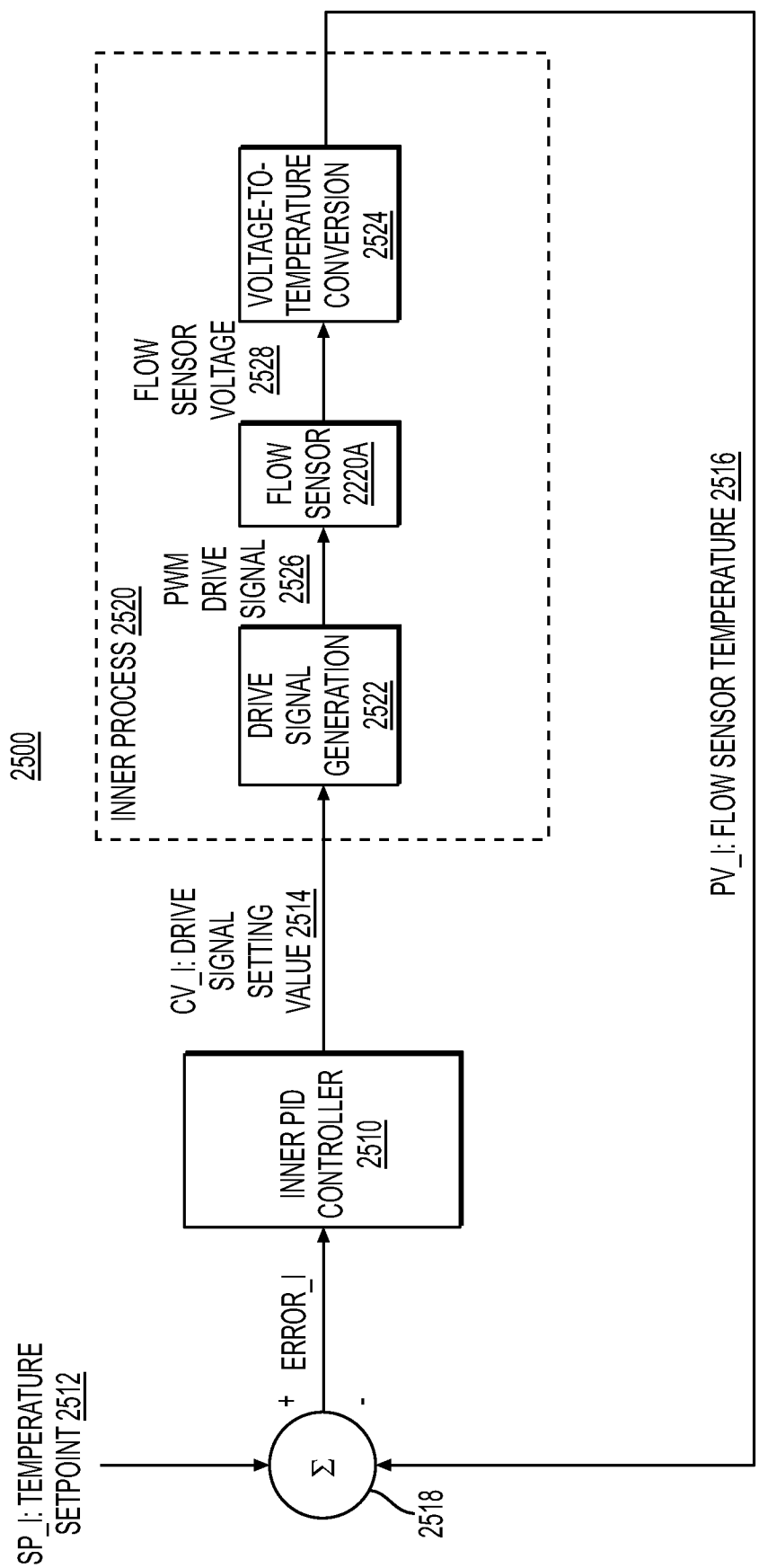
FIG. 25A is a diagram of an inner PID control loop according to an example embodiment.
Figure 25B:
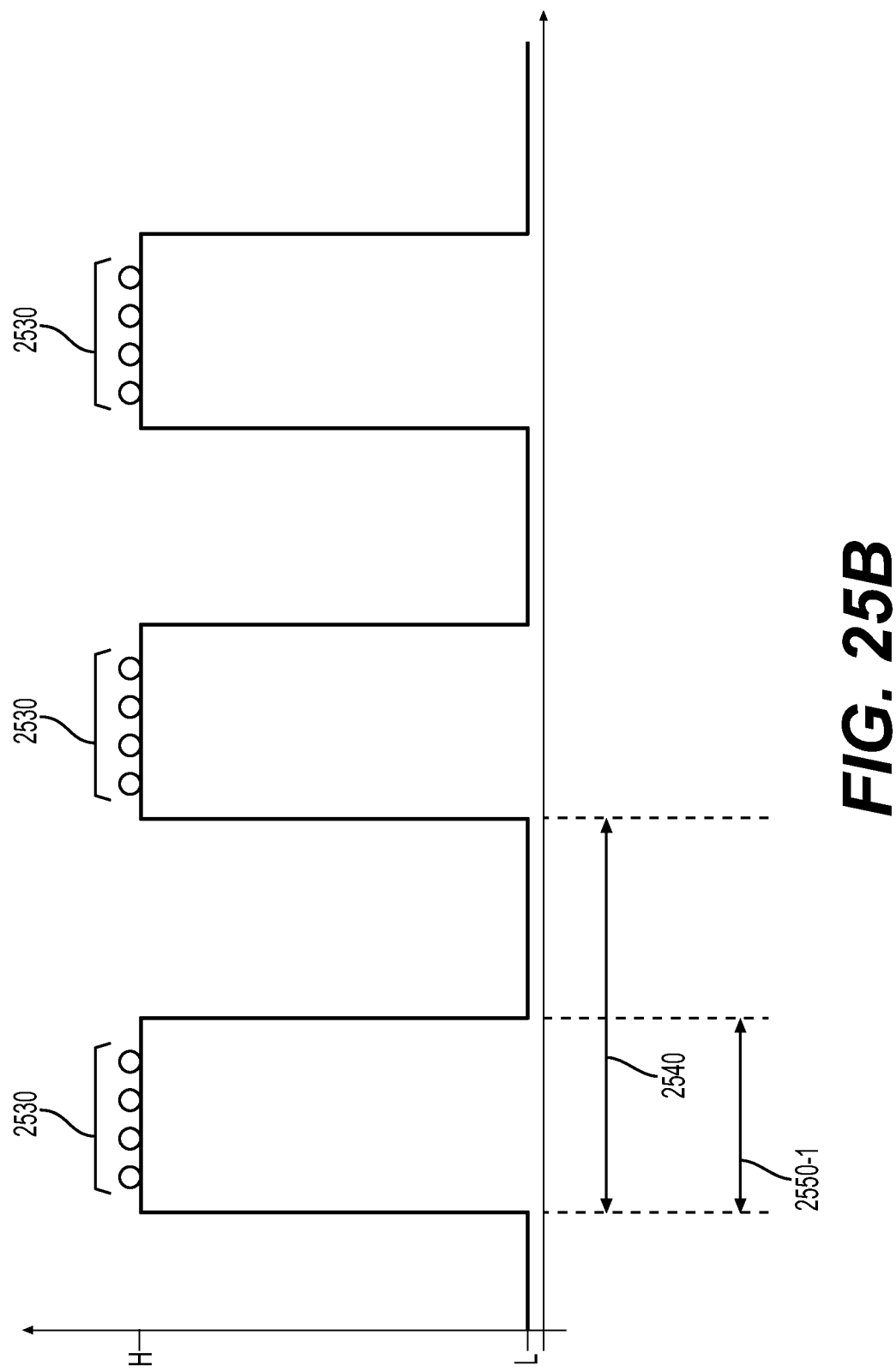
FIGS. 25B-25D illustrate example waveforms of a pulse width modulated (PWM) drive signal of FIG. 25A.
Figure 25C:
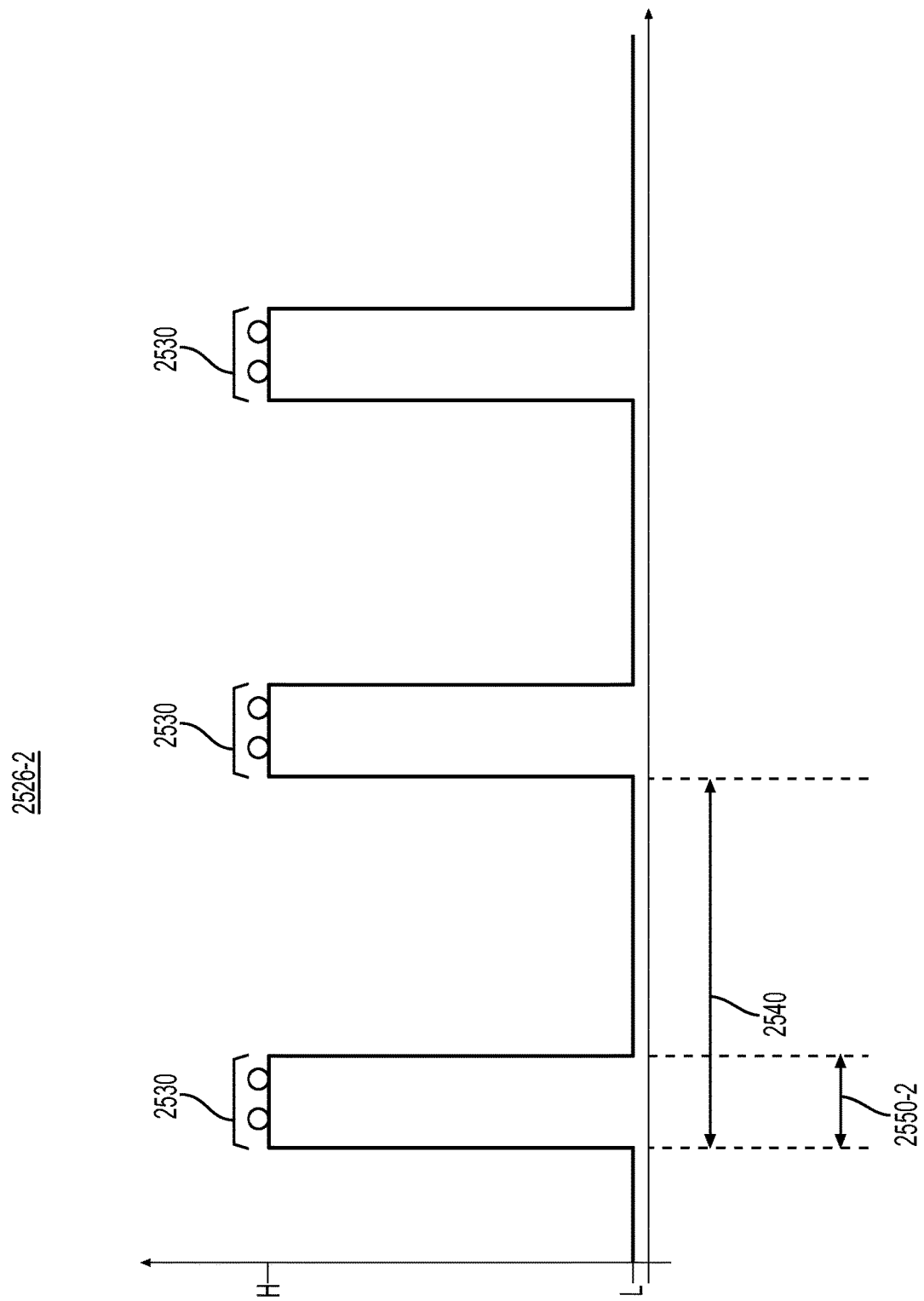
Figure 25D:
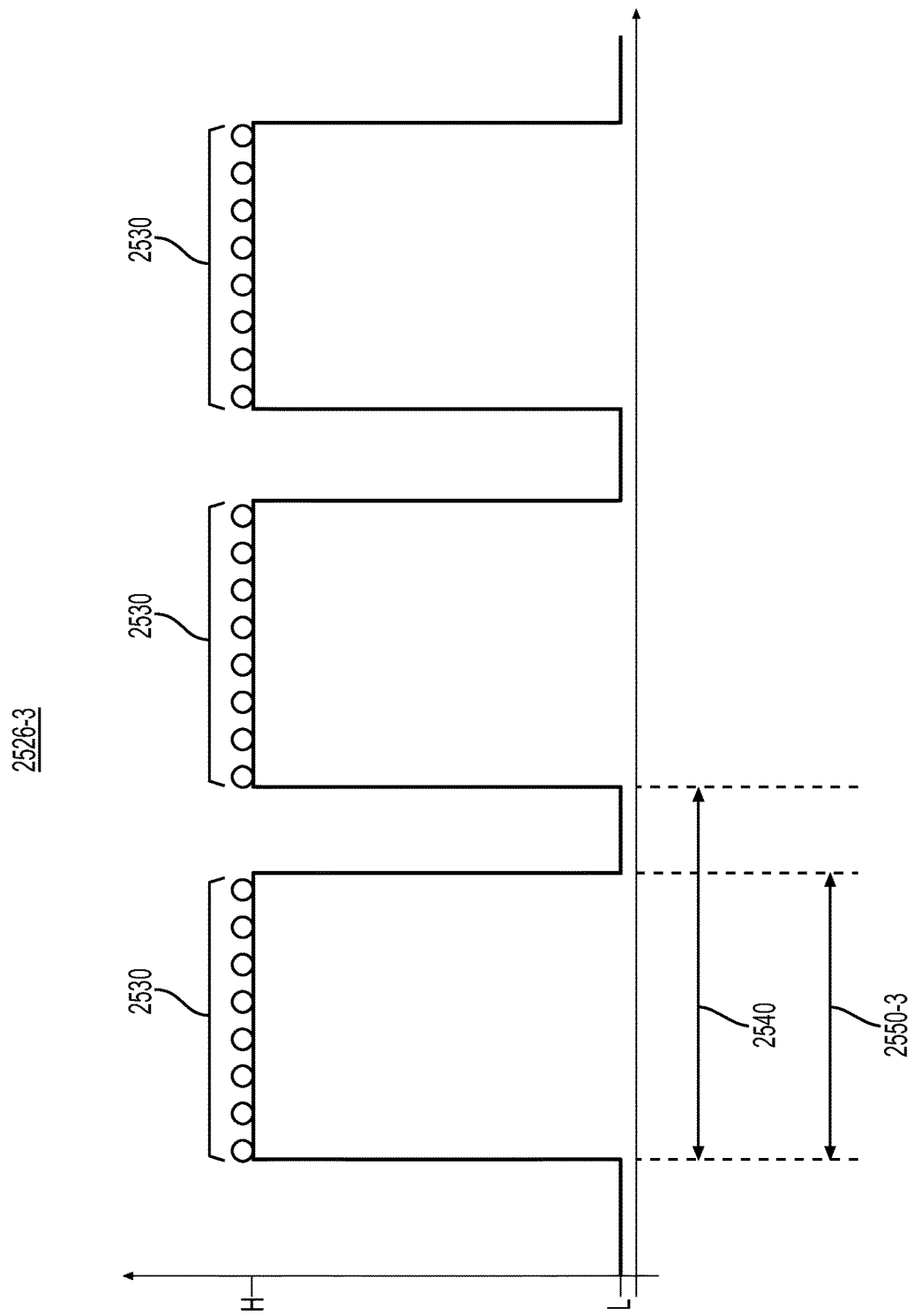
Figure 26:
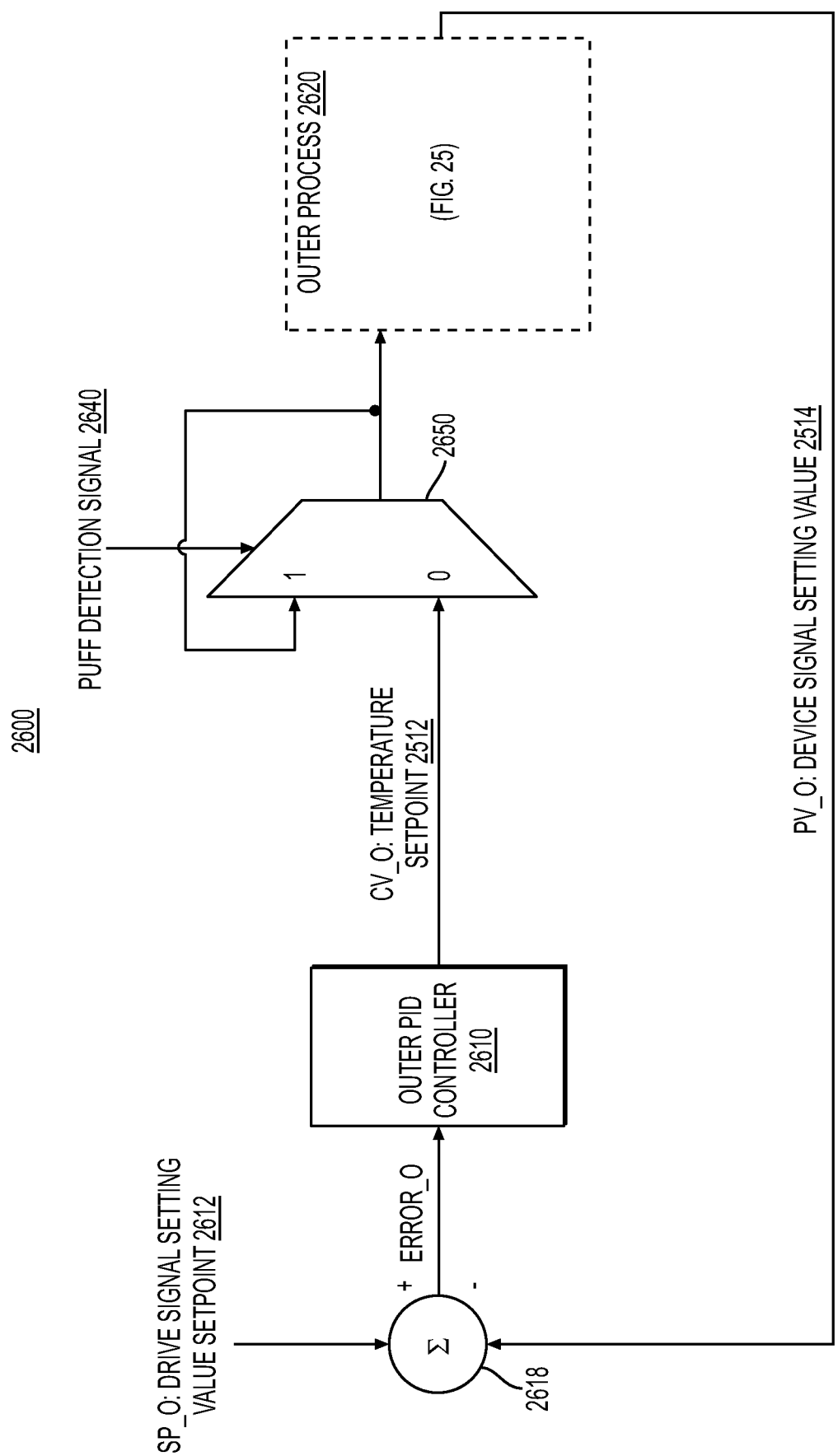
FIG. 26 is a diagram of an outer PID control loop according to an example embodiment.

FIG. 25A is a diagram of an inner PID control loop 2500, FIGS. 25B-25D illustrate first through third example waveforms 2526-1-2526-3 of a pulse width modulated (PWM) drive signal 2526 of FIG. 25A, and FIG. 26 is a diagram of an outer PID control loop 2600.

As is illustrated in FIG. 25A, the inner PID control loop 2500 calculates an inner error Error_I based on a difference between an inner setpoint SP_I and an inner process variable PV_I which is output from an inner process 2520. For example, the controller 2105 or a controller included in the pod system 2200 of the pod assembly 300 may determine the difference between an inner setpoint SP_I and an inner process variable PV_I by performing a summation operation 2518. In the example illustrated in FIG. 25A, the summation operation 2518 includes calculating, as the inner error Error_I, the sum the inner setpoint SP_I and an inverted (i.e., negative (−)) version of the inner process variable PV_I. Based on the inner error Error_I, an inner PID controller 2510 applies a correction to an inner control variable CV_I which is then applied as an input to inner process 2520 in such a manner that the inner error Error_I is reduced or, alternatively, minimized. The inner PID controller 2510 is configured to generate the control variable CV_I by using the inner error Error_I to determine a proportional term (P), an integral term (I), and a derivative term (D) in accordance with known methods. According to at least some example embodiments, the inner PID controller 2510 may be embodied by the controller 2105 within the device system 2100 of the device body 100 or as a separate controller within the pod system 2200 of the pod assembly 300. The inner process 2520 will now be discussed in greater detail below.

Referring to FIG. 25A, the inner process 2520 is a process for driving the flow sensor 2220A. According to at least some example embodiments, the inner process 2520 includes a drive signal generation function 2522, the flow sensor 2220A, and a voltage-to-temperature conversion function 2524. According to at least some example embodiments, the drive signal generation function 2522 and the voltage-to-temperature conversion function 2524 may be embodied by a controller. For example, operations described in the specification as being performed by the drive signal generation function 2522 or the voltage-to-temperature conversion function 2524 may be performed, or controlled, by the controller 2105. As another example, operations described in the specification as being performed by the drive signal generation function 2522 or the voltage-to-temperature conversion function 2524 may be performed, or controlled, by a separate controller included in the pod system 2200 of the pod assembly 300.

The flow sensor 2220A is driven by a pulse width modulated (PWM) drive signal 2526 which is generated by the drive signal generation function 2522. According to at least some example embodiments, the drive signal generation function 2522 generates the PWM drive signal 2526 and applies the PWM drive signal 2526 to the flow sensor 2220A by controlling the power supply 2110 to generate the PWM drive signal 2526 and apply the PWM drive signal to the flow sensor 2220A (e.g., via the pod electrical/data interface 2120). Applying the PWM drive signal 2526 to the flow sensor 2220A causes the heated element of the flow sensor 2220A to accumulate heat thus increasing a temperature of the heated element. For example, FIGS. 25B-25D illustrate first through third example waveforms 2526-1-2526-3 of the PWM drive signal 2526. The first through third example waveforms 2526-1-2526-3 illustrate how a magnitude of a current of the PWM drive signal 2526 varies with respect to time. In the examples shown in FIGS. 25B-25D, the vertical axes of the first through third example waveforms 2526-1-2526-3 show the magnitude of the current of the PWM drive signal 2526, which may be expressed, for example, in amps (A) or milliamps (mA). In the examples shown in FIGS. 25B-25D, the horizontal axes of the first through third example waveforms 2526-1-2526-3 show time, which may be expressed, for example, in seconds (s) or milliseconds (ms). As is illustrated in FIGS. 25B-25D, according to at least some example embodiments, the PWM drive signal 2526 is a periodic signal that oscillates between a high value (H) and a low value (L). In the examples illustrated in FIGS. 25B-25D, first through third example waveforms 2526-1-2526-3 share the same period, common period 2540, while first through third duty cycles 2550-1-2550-3 of the first through third example waveforms 2526-1-2526-3, respectively, are different from one another.

Returning to FIG. 25A, the drive signal setting value 2514 controls a level of power applied to (and, thus, an amount of heat generated by) the heated element of the flow sensor 2220A by controlling a duty cycle of the PWM drive signal 2526 generated by the drive signal generation function 2522. For example, according to at least some example embodiments, the drive signal generation function 2522 generates the PWM drive signal 2526 in such a manner that the duty cycle of the PWM drive signal 2526 increases as the drive signal setting value 2514 output from the inner PID controller 2510 to the drive signal generation function 2522 increases, and the duty cycle of the PWM drive signal 2526 decreases as the drive signal setting value 2514 output from the inner PID controller 2510 to the drive signal generation function 2522 decreases.

For example, according to at least some example embodiments, the inner PID controller 2510 may generate the drive signal setting value 2514 to be within an upper limit and a lower limit, and the drive signal generation function 2522 may generate the PWM drive signal 2526 in such a manner that the duty cycle of the PWM drive signal 2526 is proportional to the drive signal setting value 2514. For example, as is illustrated in FIGS. 25B-25D, the first duty cycle 2550-1 of the first example waveform 2526-1 of FIG. 25B corresponds to approximately 50% of the common period 2540, the second duty cycle 2550-2 of the second example waveform 2526-2 of FIG. 25C corresponds to approximately 25% of the common period 2540, and the third duty cycle 2550-3 of the third example waveform 2526-3 of FIG. 25C corresponds to approximately 75% of the common period 2540. Thus, in an example scenario in which an upper limit and lower limit of the drive signal setting value 2514 are 10.0 and 0.0, respectively, the drive signal generation function 2522 may generate the first duty cycle 2550-1 of the first example waveform 2526-1 of FIG. 25B in response to the drive signal setting value 2514 being 5.0, generate the second duty cycle 2550-2 of the second example waveform 2526-2 of FIG. 25C in response to the drive signal setting value 2514 being 2.5, and generate the third duty cycle 2550-3 of the third example waveform 2526-3 of FIG. 25C in response to the drive signal setting value 2514 being 7.5. While, 10.0 and 0.0 are provided as examples of an upper limit and lower limit of the drive signal setting value 2514, respectively, the upper and lower limits of the drive signal setting value 2514 are not limited to the values 10.0 and 0.0, and may be set to any values.

Returning to FIG. 25A, when a level of the PWM drive signal 2526 is high, a voltage of the flow sensor 2220A, flow sensor voltage 2528, may be measured. For example, FIGS. 25B-25D each show samples 2530. According to at least some example embodiments, samples 2530 each illustrate an example timing of an operation of sampling the flow sensor voltage 2528. According to at least some example embodiments, the sampling of the flow sensor voltage 2528 may be performed or controller by the controller 2105 or a controller included in the pod system 2200 of the pod assembly 300. According to at least some example embodiments, as is illustrated in FIGS. 25B-25D, samples 2530 may occur periodically while a level of the PWM drive signal 2526 is high (H), and samples 2530 may not occur while a level of the PWM drive signal 2526 is low (L). According to at least some example embodiments, a current of the PWM drive signal 2526 when high (H) is known and a relationship between a temperature and resistance of the heated element of the flow sensor 2220A is also known. Thus, in accordance with known methods (e.g., utilizing Ohm's law), the voltage-to-temperature conversion function 2524 converts the flow sensor voltage 2528 into flow sensor temperature 2516.

Thus, the process being controlled by the inner PID control loop 2500 is the inner process 2520, the inner setpoint SP_I is a temperature setpoint 2512, the inner control variable CV_I is the drive signal setting value 2514, and the inner process variable PV_I is the flow sensor temperature 2516.

Consequently, the inner PID control loop 2500 of FIG. 25A operates to continuously correct the drive signal setting value 2514 (thereby changing a duty cycle of the PWM drive signal 2526, and thus, an amount of heat generated by the heated element of the flow sensor 2220A) so as to reduce or, alternatively, minimize a difference between the flow sensor temperature 2516 and the temperature setpoint 2512. As a flow rate of air passing through and/or across the heating element of the flow sensor 2220A increases, a rate at which heat is extracted from the heating element by the flowing air increases. As a rate at which heat is extracted from the heating element by the flowing air increases, so does a level of power that should be applied to the heated element so as to maintain a temperature of the heated element at the temperature setpoint 2512. Consequently, by measuring or estimating a level of power being applied to the heated element of the flow sensor 2220A, the nicotine e-vaping device 500 (e.g., the controller 2105 and/or a controller of the pod system 2200) can measure or estimate a flow rate of air passing around the heating element of the flow sensor 2220A, thereby measuring or estimating a flow rate of air passing through the nicotine e-vaping device 500 and/or pod assembly 300.

However, a performance of the flow sensor 2220A may be negatively affected when an ambient temperature of the flow sensor 2220A changes while the temperature setpoint 2512 remains fixed. For example, in a scenario in which the ambient temperature of the flow sensor 2220A increases, the temperature of the heated element of the flow sensor 2220A may also increase, for example, due to the heated element receiving heat from the air in the immediate vicinity of the heated element. As the temperature of the heated element increases, so does the resistance (Ω) of the heated element. Thus, values of both the flow sensor voltage 2528 measured from the flow sensor 2220A and the flow sensor temperature 2516 generated by the voltage-to-temperature conversion function 2524 rise as well. Further, if, for example, the flow sensor temperature 2516 exceeds the temperature setpoint 2512, the resulting value of the inner error Error_I will cause the inner PID controller 2510 to attempt to lower the flow sensor temperature 2516 by reducing a level of the power applied to the heated element of the flow sensor 2220A (i.e., by reducing the drive signal setting value 2514 so as to reduce the duty cycle of the PWM drive signal 2556). Accordingly, if inner error Error_I is large enough to cause the inner PID controller 2510 to attempt to reduce the level of power applied to the heated element below a level necessary for the flow sensor 2220A to function reliably, the flow sensor 2220A may become unresponsive due to lack of power, and thus, cease to perform a flow sensing function. For example, if the inner PID controller 2510 reduces the drive signal setting value 2514 to a point where the resulting duty cycle of the PWM drive signal 2556 is too low to provide a sufficient amount of power to the flow sensor 2220A, the flow sensor 2220A may become unresponsive due to lack of power, and thus, cease to perform a flow sensing function.

Consequently, in order to avoid the scenario discussed above in which the flow sensor 2220A ceases to function properly, it may be beneficial to change the temperature setpoint 2512 of the inner PID control loop 2500 of FIG.

25A in accordance with a change in the ambient temperature of flow sensor 2220A. One solution would be to employ a separate temperature sensor dedicated to detecting the ambient temperature of the flow sensor 2220A.

However, according to at least some example embodiments, a dual control loop architecture that includes the outer PID control loop 2600 of FIG. 26, in conjunction with the inner PID control loop 2500 of FIG. 25A discussed above, is capable of tracking changes in ambient temperature of the flow sensor 2220A and adjusting the temperature setpoint 2512 accordingly. The outer PID control loop 2600 of FIG. 26 will now be discussed in greater detail below.

Referring to FIG. 26, the outer PID control loop 2600 calculates an outer error Error_O based on a difference between an outer setpoint SP_O and an outer process variable PV_O which is output from an outer process 2620. For example, the controller 2105 or a controller included in the pod system 2200 of the pod assembly 300 may determine the difference between the outer setpoint SP_O and the outer process variable PV_O by performing a summation operation 2618. In the example illustrated in FIG. 26, the summation operation 2618 includes calculating, as the outer error Error_O, the sum the inner setpoint SP_I and an inverted (i.e., negative (−)) version of the outer process variable PV_O. Based on the outer error Error_O, an outer PID controller 2610 applies a correction to an outer control variable CV_O which is then applied as an input to outer process 2620 in such a manner that the outer error Error_O is reduced or, alternatively, minimized. As was discussed above with reference to the inner PID controller 2510 of the inner PID control loop 2500 of FIG. 25A, the outer PID controller 2610 is configured to generate the outer control variable CV_O by using the outer error Error_O to determine a proportional term (P), an integral term (I), and a derivative term (D) in accordance with known methods. According to at least some example embodiments, the outer PID controller 2610 may be embodied by the controller 2105 within the device system 2100 of the device body 100 or as a separate controller within the pod system 2200 of the pod assembly 300. According to at least some example embodiments, the inner PID controller 2510 and the outer PID controller 2610 may both be embodied by the controller 2105 within the device system 2100 of the device body 100, both be embodied the same single controller within the pod system 2200 of the pod assembly 300, or may each be embodied as a separate controller, for example, as two controllers within the pod system 2200 of the pod assembly 300.

As is illustrated in FIG. 26, according to at least some example embodiments, the process being controlled by the outer PID control loop 2600, the outer process 2620, is the inner PID control loop 2500 of FIG. 25A. For example, as is illustrated in FIG. 26, the outer setpoint SP_O of the outer PID control loop 2600 is drive signal setting value setpoint 2612, the outer control variable CV_O of the outer PID control loop 2600 is the temperature setpoint 2512 of the inner PID control loop 2500, and the outer process variable PV_O of the outer PID control loop 2600 is the drive signal setting value 2514 of the inner PID control loop 2500.

Consequently, the outer PID control loop 2600 of FIG. 26 operates to continuously correct the temperature setpoint 2512 input into the inner PID control loop 2500 so as to reduce or, alternatively, minimize a difference between the drive signal setting value 2514 output by the inner PID control loop 2500 and the drive signal setting value setpoint 2612. Further, according to at least some example embodiments, the outer PID control loop 2600 does not adjust the temperature setpoint 2512 input into the inner PID control loop 2500 during a puff. For example, as is illustrated in FIG. 26, the outer PID control loop 2600 may include a multiplexer 2650. According to at least some example embodiments, the functions of the multiplexer 2650 may be performed by the controller 2105 or a controller included in the pod system 2200 of the pod assembly 300. Further, as is illustrated in FIG. 26, when a puff detection signal 2640 has a first logical value (e.g., logic high) indicating that a puff is occurring (i.e., indicating that a nicotine vapor is currently being drawn through outlets of the nicotine e-vaping device 500 or pod assembly 300, or a negative pressure is currently being applied to outlets of the nicotine e-vaping device 500 or pod assembly 300) a present value of the temperature setpoint 2512 input into the multiplexer 2650 becomes fixed as the value provided to the inner PID control loop 2500 until the puff detection signal 2640 transitions to a second logical value (e.g., logic low) indicating that a puff is not presently occurring (i.e., indicating that a nicotine vapor is not currently being drawn through outlets of the nicotine e-vaping device 500 or pod assembly 300, or a negative pressure is not currently being applied to outlets of the nicotine e-vaping device 500 or pod assembly 300). When the puff detection signal 2640 transitions to a second logical value (e.g., logic low) indicating that a puff is not presently occurring, the multiplexer 2650 simply outputs the temperature setpoint 2512 which is output by the outer PID controller 2610 as input to the inner PID control loop 2500. Thus, the inner setpoint SP_I of the inner PID control loop 2500 (i.e., the temperature setpoint 2512) has a fixed value while a puff is occurring, and a variable value while a puff is not occurring. The manner in which the temperature setpoint 2512 varies when a puff is not occurring will now be discussed in greater detail below. As is discussed in greater detail below with reference to FIG. 27, the puff detection signal 2640 may be generated by a puff detection signal generator. According to at least some example embodiments, the puff detection signal generator is a controller (e.g., the controller 2105 or a controller within the pod system 2200 of the pod assembly 300).

As the ambient temperature of the flow sensor 2220A rises, the drive signal setting value 2514 may fall in the manner discussed above with reference to FIG. 25A. However, the outer PID controller 2610 can prevent the drive signal setting value 2514 from falling to the point where the flow sensor 2220A may become unresponsive. For example, referring to FIG. 26, as the drive signal setting value 2514 falls relative to a drive signal setting value setpoint 2612, a magnitude of the outer error Error_O increases. In response, the outer PID controller 2610 operates to reduce the outer error Error_O by increasing the temperature setpoint 2512 in accordance with a change in the ambient temperature of the flow sensor 2220A, thereby causing the drive signal setting value 2514 to rise. For example, the inner PID controller 2510 will increase the drive signal setting value 2514 in response to the increased temperature setpoint 2512 because additional power will need to be applied to the heated element of the flow sensor 2220A in order to raise the temperature of the heated element to the newly raised temperature setpoint 2512.

In addition to raising the temperature setpoint 2512 in response to an ambient temperature of the flow sensor 2220A increasing, as is discussed in the example scenario above, the outer PID control loop 2600 may also lower the temperature setpoint 2512 in response to an ambient temperature of the flow sensor 2220A decreasing. For example, in a scenario in which the ambient temperature of the flow sensor 2220A decreases, the temperature of the heated element of the flow sensor 2220A may also decrease, for example, due to the heated element losing heat to the air in the immediate vicinity of the heated element. As the temperature of the heated element decreases, so does the resistance of the heated element. Thus, values of both the flow sensor voltage 2528 measured from the flow sensor 2220A and the flow sensor temperature 2516 generated by the voltage-to-temperature conversion function 2524 decrease as well. Further, if, for example, the flow sensor temperature 2516 is below the temperature setpoint 2512, the resulting value of the inner error Error_I will cause the inner PID controller 2510 to attempt to raise the flow sensor temperature 2516 by increasing a level of the power applied to the heated element of the flow sensor 2220A (i.e., by increasing the drive signal setting value 2514 so as to increase the duty cycle of the PWM drive signal 2556). Further, as the drive signal setting value 2514 rises relative to the drive signal setting value setpoint 2612, a magnitude of the outer error Error_O increases. In response, the outer PID controller 2610 operates to reduce the magnitude of the outer error Error_O by decreasing the temperature setpoint 2512 in accordance with a change in the ambient temperature of the flow sensor 2220A, thereby causing the drive signal setting value 2514 to fall. For example, the inner PID controller 2510 will decrease the drive signal setting value 2514 in response to the decreased temperature setpoint 2512 because a level of power applied to the heated element of the flow sensor 2220A will need to be reduced in order to lower the temperature of the heated element to the newly decreased temperature setpoint 2512.

According to at least some example embodiments, a level of the drive signal setting value setpoint 2612 may be set in accordance with the preferences of a designer and/or manufacturer of the nicotine e-vaping device 500 and/or pod assembly 300. According to at least some example embodiments, a level of the drive signal setting value setpoint 2612 may be stored in accordance with the preferences of a designer and/or manufacturer of the nicotine e-vaping device 500 (e.g., in the device body 100 and/or the pod assembly 300). For example, according to at least some example embodiments, a level of the drive signal setting value setpoint 2612 may be set in accordance with a desired margin between an ambient temperature of the HWA 2220A and a temperature of the heated element of the HWA 2220A (i.e., when a puff in not occurring).

Consequently, the outer PID control loop 2600 can advantageously use the flow sensor 2220A to control the temperature setpoint 2512 to change in accordance with changes in the ambient temperature of the flow sensor 2220A without the need to implement a separate temperature sensor (e.g., within the pod assembly 300) for detecting the ambient temperature of the flow sensor 2220A. An example method of operating a HWA according to at least some example embodiments will now be explained below with reference to FIG. 27.

Figure 27:
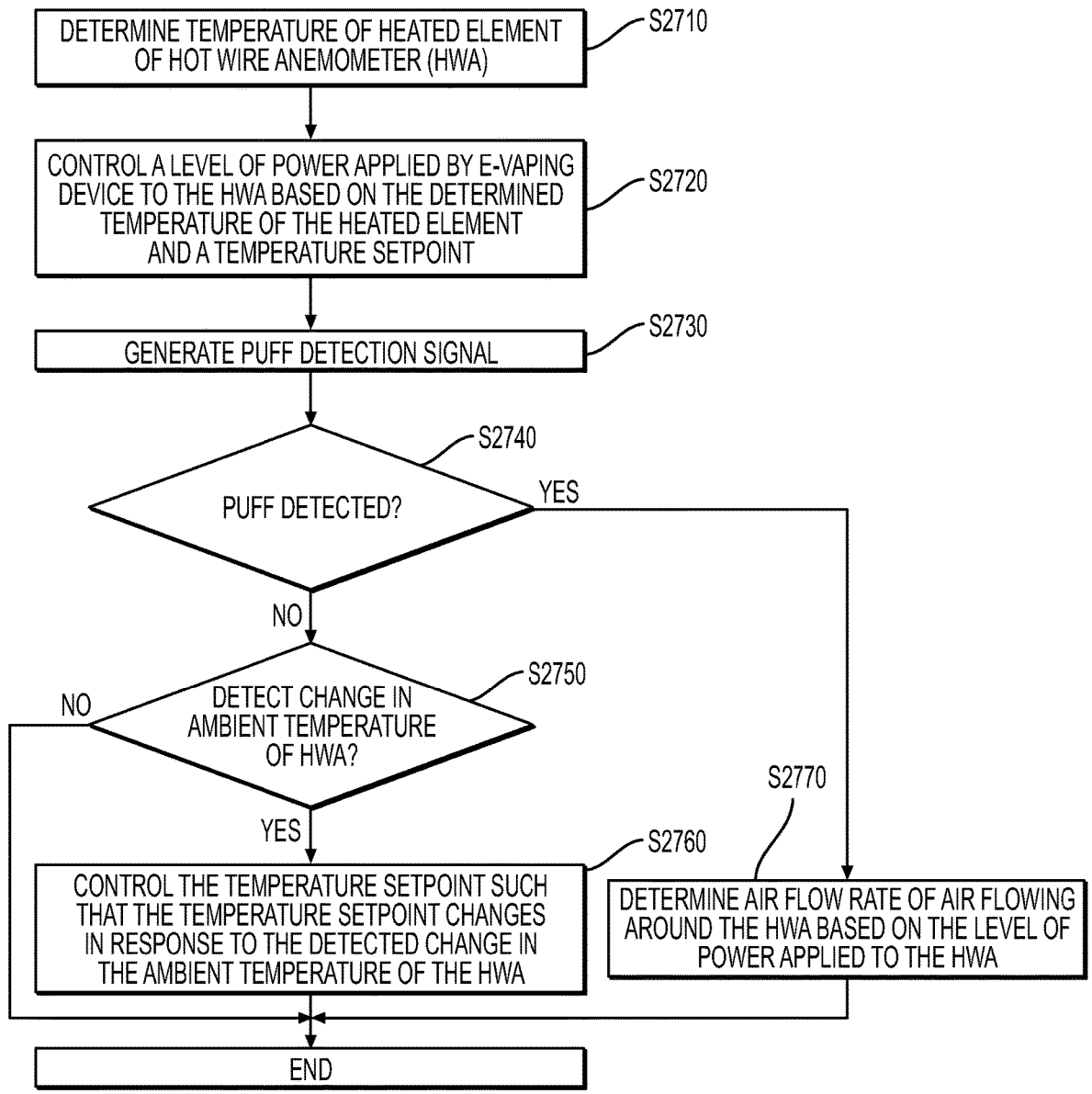
FIG. 27 is a flow chart illustrating a method of operating a HWA according to an example embodiment.

FIG. 27 is a flow chart illustrating a method of operating a HWA according to at least some example embodiments.

Referring to FIG. 27, in step S2710, a temperature of the heated element of a HWA is determined. For example, as is discussed above with reference to FIG. 25A, a controller (e.g., the controller 2105 or a controller included in the pod system 2200 of the pod assembly 300) may perform or control an operation of measuring the flow sensor voltage 2528, and the voltage-to-temperature conversion function 2424 may convert the measured flow sensor voltage 2528 into the flow sensor temperature 2516, which represents a temperature of the heated element of the HWA 2220A.

In step S2720, a level of power applied by the nicotine e-vaping device to the HWA is controlled based on the determined temperature of the heated element of the HWA and a temperature setpoint. For example, as is discussed above with reference to FIG. 25A, the inner PID controller 2510 generates the drive signal setting value 2514 (i.e., the inner control variable CV_I) based on a difference between the temperature setpoint 2512 (i.e., the inner setpoint SP_I) and the flow sensor temperature 2516 (i.e., the inner process variable PV_I). Further, the drive signal setting value 2514 controls a level of a level of power applied to the heated element of the flow sensor 2220A by, for example, controlling a duty cycle of the PWM drive signal 2526.

In step S2730, a puff detection signal is generated. According to at least some example embodiments, the puff detection signal 2640 may be generated by a controller (e.g., the controller 2105 or a controller included in the pod system 2200 of the pod assembly 300) by monitoring the drive signal setting value 2514 and/or a gradient of the drive signal setting value 2514. For example, in step S730, while the puff detection signal 2640 has a value indicating that a puff is not presently occurring (e.g., a logic low value or 0), the controller may change the value of the puff detection signal 2640 to a value indicating that a puff is presently occurring (e.g., a logic high value or 1) in response to determining that a present level (or average level over a sliding window of levels) of the drive signal setting value 2514 has exceeded a puff start level threshold and/or determining that a present gradient (or average gradient over a sliding window of gradients) of the drive signal setting value 2514 has exceeded a puff start gradient threshold. Further, in step S730, while the puff detection signal has a value indicating that a puff is presently occurring (e.g., a logic high value or 1), the controller may change the value of the puff detection signal 2640 to a value indicating that a puff is not presently occurring (e.g., a logic low value or 0) in response to determining that a present level (or average level over a sliding window of levels) of the drive signal setting value 2514 has fallen below a puff end level threshold and/or determining that a present gradient (or average gradient over a sliding window of gradients) of the drive signal setting value 2514 has fallen below a puff end gradient threshold.

In step S2740, a determination is made with respect to whether or not a puff is detected. For example, if a level of the puff detection signal 2640 generated in step S2730 indicates that a puff is not detected (N), then the method proceeds to step S2750.

In step S2750, a determination is made with respect to whether or not a change in the ambient temperature of the HWA is detected. For example, in the manner discussed above with respect to FIG. 26, the outer PID controller 2610 may determine that an ambient temperature of the HWA 2220A has changed based on detecting an increase in a magnitude of the outer error Error_O. Additionally, a sign of the outer error Error_O may indicate to the outer PID controller 2610 a direction (e.g., increase or decrease) of the change of the ambient temperature of the HWA 2220A. If no change in the ambient temperature of the HWA 2220A is detected in step S2750 (N), the method ends. If a change is detected in the ambient temperature of the HWA 2220A in step S2750 (Y), the method proceeds to step S2760.

In step S2760, the temperature setpoint is controlled such that the temperature setpoint changes in response to the detected change in the ambient temperature of the HWA. For example, as is discussed above with respect to FIG. 26, the outer PID controller 2610 may respond to the change in the ambient temperature of the HWA 2220A detected in step S2750 by changing a value of the temperature setpoint 2512 in accordance with the ambient temperature of the HWA 2220A. For example, the outer PID controller 2610 may increase the temperature setpoint 2512 in response to detecting an increase in the ambient temperature of the HWA 2220A, and the outer PID controller 2610 may decrease the temperature setpoint 2512 in response to detecting a decrease in the ambient temperature of the HWA 2220A. According to at least some example embodiments, after step S2760, the method ends.

Returning to step S2750, if a level of the puff detection signal 2640 generated in step S2730 indicates that a puff is detected (Y), then the method proceeds to step S2770.

In step S2770, an air low rate of air flowing around the HWA is determined based on the level of power applied to the HWA. For example, in step S2770, a controller (e.g., the controller 2105 or a controller included in the pod system 2200 of the pod assembly 300) may determine the air flow rate of air flowing around the HWA based on the present drive signal setting value 2514. Specifically, as is discussed above, the heated element of the HWA 2220A becomes heated as a result of applying power to the heated element through the PWM drive signal 2526. Further, the temperature of the heated element affects the resistance (SI) of the heated element. Consequently, the voltage of the heated element (e.g., the flow sensor voltage 2528) may be used to estimate the temperature of the heated element (e.g., the flow sensor temperature 2516). Further, in the presence of flowing air, heat will be carried away from the heated element of the HWA 2220A by the flowing air, and thus, a level of power needed to cause the heated element of the HWA 2220A to maintain a particular temperature can be used to estimate an air flow rate of air flowing around the heated element of the HWA 2220A. Further, the level of power needed to cause the heated element of the HWA 2220A to maintain a particular temperature may be determined or estimated based on the present drive signal setting value 2514, which controls the present level of power applied to the heated element of the HWA 2220A by controlling the duty cycle of the PWM drive signal 2526 being applied to the HWA 2220A. Consequently, the controller 2105 or a controller included in the pod system 2200 may use the present drive signal setting value 2514 to determine or estimate an air flow rate of air flowing around the heated element of the HWA 2220A. Further, the air flow rate of air flowing around the heated element of the HWA 2220A may be indicative of the air flow rate of air flowing through the pod assembly 300 and/or the nicotine e-vaping device 500. For example, as is noted above with reference to FIGS. 13 and 14, during vaping, air enters the pod assembly 300 via the pod inlet 322 and exits the pod assembly via pod outlet 304. Further, as is noted above with reference to FIGS. 18-20, the sensor 364 may be or include the HWA 2220A, and thus, the HWA 2220A may situated within the converged path 330c. Further, as is also described above with reference to FIGS. 18-20, the converged path 330c is a portion of a flow path of air that is drawn into the pod assembly 300 through pod inlet 322, travels through the heating chamber (e.g., entering from module outlet 368 and exiting to the vapor channel 316), and exits the pod assembly 300 via pod outlet 304. Consequently, according to at least some example embodiments, the air that flows around the HWA 2220A is air that flows from through the pod assembly 300 of the e-vaping device 500 via the pod inlet 322 and the pod outlet 304 (e.g., during a puff), and thus, the air flow rate of air flowing around the heated element of the HWA 2220A may be indicative of the air flow rate of air flowing through the pod assembly 300 and/or the nicotine e-vaping device 500.

Thus, according to at least some example embodiments, a single HWA (e.g., HWA 2220A) in conjunction with the dual control loop architecture, which includes the inner PID control loop 2500 of FIG. 25A and the outer PID control loop 2600 of FIG. 26, may facilitate any or all of (i) air flow rate sensing, (ii) puff detection, and (iii) ambient temperature tracking for the purpose of improving the air flow rate sensing, without the need to implement an additional temperature sensor for sensing an ambient temperature of the HWA.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A method of controlling a hot wire anemometer (HWA) of a nicotine e-vaping device, the method comprising:
controlling, by a first proportional-integral-derivative (PID) controller, a level of power applied by the nicotine e-vaping device to the HWA based on a temperature of a heated element of the HWA and a temperature setpoint;
generating a puff detection signal indicating whether or not a puff is currently occurring with respect to the nicotine e-vaping device, the puff detection signal having a first logical value when the puff is occurring and a second logical value when the puff is not occurring, and the temperature setpoint being fixed while the puff detection signal has the first logical value indicating that the puff is currently occurring with respect to the nicotine e-vaping device; and
while the puff detection signal has the second logical value indicating that the puff is not currently occurring with respect to the nicotine e-vaping device,
detecting, by a second PID controller, a change in an ambient temperature of the HWA; and
controlling, by the second PID controller, the temperature setpoint such that the temperature setpoint is adjusted in response to the detected change in the ambient temperature of the HWA.

2. The method of claim 1, wherein the controlling of the level of power applied by the nicotine e-vaping device to the HWA comprises:
generating, by the first PID controller, a drive signal setting value,
the level of power applied by the nicotine e-vaping device to the HWA being based on the drive signal setting value.

3. The method of claim 2, further comprising:
while the puff detection signal indicates that the puff is currently occurring with respect to the nicotine e-vaping device, determining a flow rate of air flowing around the HWA based on the drive signal setting value.

4. The method of claim 2, wherein the generating of the puff detection signal comprises:
determining a gradient of the drive signal setting value; and
generating the puff detection signal based on the determined gradient of the drive signal setting value.

5. The method of claim 2, further comprising:
generating a pulse width modulated (PWM) drive signal based on the drive signal setting value; and
applying the level of power to the HWA by applying the PWM drive signal to the HWA.

6. The method of claim 5, wherein the generating of the PWM drive signal includes generating the PWM drive signal such that a duty cycle of the PWM is controlled based on the drive signal setting value.

7. The method of claim 2, wherein the generating of the drive signal setting value comprises:
generating, by the first PID controller, the drive signal setting value based on a difference between the temperature of a heated element of the HWA and the temperature setpoint.

8. The method of claim 7, wherein the detecting of the change in the ambient temperature of the HWA comprises:
detecting, by the second PID controller, the change in the ambient temperature of the HWA based on a difference between the drive signal setting value and a drive signal setting value setpoint.

9. The method of claim 2, wherein the detecting of the change in the ambient temperature of the HWA comprises:
detecting, by the second PID controller, the change in the ambient temperature of the HWA based on a difference between the drive signal setting value and a drive signal setting value setpoint.

10. The method of claim 9, wherein the controlling of the temperature setpoint comprises:
increasing, by the second PID controller, the temperature setpoint in response to detecting an increase in the ambient temperature of the HWA; and
decreasing, by the second PID controller, the temperature setpoint in response to detecting a decrease in the ambient temperature of the HWA.

11. A nicotine e-vaping device, comprising:
a nicotine pre-vapor formulation storage portion for storing a nicotine pre-vapor formulation;
a heater configured to generate a nicotine vapor by heating the nicotine pre-vapor formulation;
a hot wire anemometer (HWA);
a first proportional-integral-derivative (PID) controller configured to control a level of power applied by the nicotine e-vaping device to the HWA based on a temperature of a heated element of the HWA and a temperature setpoint;
a puff detection signal generator configured to generate a puff detection signal indicating whether or not a puff is currently occurring with respect to the nicotine e-vaping device, the puff detection signal having a first logical value when the puff is occurring and a second logical value when the puff is not occurring, and the temperature setpoint being fixed while the puff detection signal has the first logical value indicating that the puff is currently occurring with respect to the nicotine e-vaping device; and
a second PID controller configured such that, while the puff detection signal has the second logical value indicating that the puff is not currently occurring with respect to the nicotine e-vaping device,
the second PID controller detects a change in an ambient temperature of the HWA, and
the second PID controller controls the temperature setpoint such that the temperature setpoint is adjusted in response to the detected change in the ambient temperature of the HWA.

12. The nicotine e-vaping device of claim 11, wherein the first PID controller is configured to control the level of power applied by the nicotine e-vaping device to the HWA by generating a drive signal setting value, the level of power applied by the nicotine e-vaping device to the HWA being based on the drive signal setting value.

13. The nicotine e-vaping device of claim 12, wherein the second PID controller is further configured to determine a flow rate of air flowing around the HWA based on the drive signal setting value, while the puff detection signal indicates that a puff is currently occurring with respect to the nicotine e-vaping device.

14. The nicotine e-vaping device of claim 12, wherein the puff detection signal generator is configured to,
determine a gradient of the drive signal setting value, and
generate the puff detection signal based on the determined gradient of the drive signal setting value.

15. The nicotine e-vaping device of claim 12, further comprising:
a drive signal generator configured to,
generate a pulse width modulated (PWM) drive signal based on the drive signal setting value, and
apply the level of power to the HWA by applying the PWM drive signal to the HWA.

16. The nicotine e-vaping device of claim 15, wherein the drive signal generator is configured to control a duty cycle of the PWM drive signal based on the drive signal setting value.

17. The nicotine e-vaping device of claim 12, wherein the first PID controller is configured to generate the drive signal setting value based on a difference between the temperature of a heated element of the HWA and the temperature setpoint.

18. The nicotine e-vaping device of claim 17, wherein the second PID controller is configured to detect the change in the ambient temperature of the HWA based on a difference between the drive signal setting value and a drive signal setting value setpoint.

19. The nicotine e-vaping device of claim 12, wherein the second PID controller is configured to detect the change in the ambient temperature of the HWA based on a difference between the drive signal setting value and a drive signal setting value setpoint.

20. The nicotine e-vaping device of claim 19, wherein the second PID controller is configured to control the temperature setpoint by,
increasing the temperature setpoint in response to detecting an increase in the ambient temperature of the HWA, and
decreasing the temperature setpoint in response to detecting a decrease in the ambient temperature of the HWA.

* * * * *